US012433739B2

(12) United States Patent
Rassman et al.

(10) Patent No.: US 12,433,739 B2
(45) Date of Patent: Oct. 7, 2025

(54) HAIR TRANSPLANTATION SURGERY WITH GRAFT-ON-DEMAND PROCESSING OF FOLLICULAR UNITS

(71) Applicant: EnGraft Technologies, Inc., Corona Del Mar, CA (US)

(72) Inventors: William R Rassman, Los Angeles, CA (US); Pascal Boudjema, Paris (FR)

(73) Assignee: EnGraft Technologies, Inc., Marina del Rey, CA (US)

( * ) Notice: Subject to any disclaimer, the term of this patent is extended or adjusted under 35 U.S.C. 154(b) by 0 days.

(21) Appl. No.: 18/659,969

(22) Filed: May 9, 2024

(65) Prior Publication Data

US 2025/0041045 A1 Feb. 6, 2025

Related U.S. Application Data

(60) Provisional application No. 63/516,264, filed on Jul. 28, 2023.

(51) Int. Cl.
*A61B 34/30* (2016.01)
*A61B 17/00* (2006.01)
(Continued)

(52) U.S. Cl.
CPC .......... *A61F 2/10* (2013.01); *A61B 17/32053* (2013.01); *A61B 34/10* (2016.02);
(Continued)

(58) Field of Classification Search
CPC ........... A61F 2/10; A61B 34/10; A61B 34/30; A61B 90/14; A61B 17/32053;
(Continued)

(56) References Cited

U.S. PATENT DOCUMENTS 5,827,297 A 10/1998 Boudjema
6,572,625 B1 6/2003 Rassman
(Continued)

FOREIGN PATENT DOCUMENTS

WO 2015/186146 12/2015

OTHER PUBLICATIONS

Venus Concept , NeoGraft® Hair Restoration System, Jul. 10, 2023.
(Continued)

*Primary Examiner* — Ashley L Fishback
(74) *Attorney, Agent, or Firm* — Venable LLP

(57) ABSTRACT

The harvesting of hair for a hair transplant procedure with immediate placement of the hair grafts to the balding area, employs a hollow drill connected to a suction with an imaging system (containing one or more cameras) which permits alignment of the center of the cutting edge of the needle on or slightly offset from the axis of the hair within the follicular unit to be removed. This harvesting tool may be robotically controlled. As each follicular unit may have more than one hair, the surgeon controls the number of hairs in each graft he wishes to remove, excising the graft one at a time. A special FUE tool is used that excises the entire follicular unit with minimal residual attachments. The tool utilizes vacuum to facilitate complete excision. The graft that is excised is sucked though tubing and almost instantaneously delivered to an implanter held by the surgeon (Duplex Implanter) or by a robot. This graft on Demand system is controlled by the surgeon through a series of commands to the handpiece of the implanter for one, two, three or more hair grafts. The excision needle (punch) is placed to remove a hair graft with the chosen number of hairs, taken from an area which has been previously mapped out. When properly aligned, a follicular unit is removed without damaging critical anatomical portions of the fol-
(Continued)

licles and it is delivered to the implanter at the command of the surgeon. In one embodiment, a movable x/y/z stabilizing gantry is employed to position the hollow needle in each instance which can be manually controlled by the surgeon, or robotically controlled with one or more robots. In another embodiment, a computer maps out the location of every graft within the surgical field of view, in part or in whole, and selects those follicles, minimizing the spacing left remaining after each excision while obtaining the number of grafts targeted by the surgeon. In still another embodiment, one or more robotic arms, controlled automatically by a controller or manually by a surgeon, operate graft excision instruments to facilitate speed and accuracy of the excision process.

19 Claims, 19 Drawing Sheets

(51) Int. Cl.

| | |
|---|---|
| ***A61B 17/3205*** | (2006.01) |
| ***A61B 34/10*** | (2016.01) |
| ***A61B 34/20*** | (2016.01) |
| ***A61B 90/14*** | (2016.01) |
| ***A61F 2/10*** | (2006.01) |
| *A61B 90/00* | (2016.01) |

(52) U.S. Cl.
CPC .............. *A61B 34/30* (2016.02); *A61B 90/14* (2016.02); *A61B 2017/00119* (2013.01); *A61B 2017/00203* (2013.01); *A61B 2017/00752* (2013.01); *A61B 2017/00862* (2013.01); *A61B 2017/00973* (2013.01); *A61B 2017/00991* (2013.01); *A61B 2034/2057* (2016.02); *A61B 2090/3991* (2016.02); *A61B 2217/005* (2013.01); *A61B 2217/007* (2013.01)

(58) Field of Classification Search
CPC .... A61B 2034/2057; A61B 2090/3991; A61B 2017/00119; A61B 2017/00203; A61B 2017/00752; A61B 2017/00862; A61B 2017/00973; A61B 2017/00991; A61B 2217/005; A61B 2217/007
See application file for complete search history.

(56) References Cited

U.S. PATENT DOCUMENTS

| | | | | |
|---|---|---|---|---|
| 8,211,134 | B2 * | 7/2012 | Oostman, Jr. | A61F 2/10 606/187 |
| 8,545,517 | B2 | 10/2013 | Bodduluri et al. | |
| 8,562,627 | B2 * | 10/2013 | DuBois | A61F 2/10 606/133 |
| 9,913,610 | B2 | 3/2018 | Bodduluri et al. | |
| 10,327,850 | B2 | 6/2019 | Bodduluri et al. | |
| 10,449,033 | B2 | 10/2019 | Silva Ramos et al. | |
| 10,537,396 | B2 | 1/2020 | Zingaretti et al. | |
| 10,548,629 | B2 | 2/2020 | Damar et al. | |
| 10,736,662 | B2 | 8/2020 | Oostman, Jr. | |
| 11,045,306 | B1 | 6/2021 | Boudjema et al. | |
| 2009/0306680 | A1 * | 12/2009 | Qureshi | A61B 90/361 606/133 |
| 2012/0179189 | A1 | 7/2012 | Zingaretti et al. | |
| 2014/0155912 | A1 | 6/2014 | Bodduluri et al. | |
| 2016/0030134 | A1 | 2/2016 | Shapter et al. | |
| 2017/0065291 | A1 | 3/2017 | Lewallen | |
| 2019/0247089 | A1 | 8/2019 | Lin et al. | |
| 2021/0059754 | A1 | 3/2021 | Kasprzak | |
| 2021/0290329 | A1 * | 9/2021 | Russell | A61B 17/3421 |
| 2022/0346896 | A1 | 11/2022 | Said et al. | |

OTHER PUBLICATIONS medic-equipments.com, Medicamat Neograft Punch Hair Matic, Jul. 10, 2023.
Calvitron Hair Transplant System, Medicament S.A., 1994.
International Search Report and Written Opinion dated Dec. 31, 2024 in counterpart application PCT/US2024/039624.

* cited by examiner

Create Hairline with Patient

Computer/camera Assess Hair Thickness, # Hairs, # Hairs/graft, Distribution by Area Defined by MD Anesthesia Administered Locally The Patient is Placed in Special Chair with a Breast Plate to Allow the Patient to Lean into the Breast Plate. As an Extension of the Breast Plate of the Chair (Somewhat like a Massage Table, See Figure), are Extension Arms that Extend Upward to the Level of the Patient's Forehead. These Arms are Bowed in Such a Manner as to Not Interfere with Access to the Recipient Area of the Head. A Tensioning Belt is Connected to these Arms to Stabilize the Patient's Head. The Area in Front of the Face may have a Viewing Area where Virtual Reality Viewing in Front of Eyes can be Used to Watch Movies, etc. During the Procedure Thumbtack Fiducial Tines (TTFT) are Placed throughout the Peripheral Donor Area for Fiducials that will Allow the Computer and Optical Equipment to Map out the Donor Area. These TTFTs will Remain in Place until all of the Graft Extractions are Complete. This will Allow the Computer to Map the Exact Location of each and every Follicular Group (Graft) within the Donor Area Before and After they are Excised. These Fiducials will be Placed by the Surgeon Once the Patient is Placed into the Special Chair and the Headband has been Connected to the Special Chair. At the End of the Graft Extraction Process, these TTFTs may be Removed by the Surgeon The Surgeon Views a Large Computer Monitor that Displays Video Information Needed to Assess and Reassess the Donor Area as the FUE Progresses. A Baseline Measurement is Fixed and Displayed in One Area of the Monitor. The Surgeon will Divide the Donor Area into Zones, so that the Video Display is Mapping the Donor Supply, Both Globally or by Regional/Zonal Measurement. This is a Dynamic Process. There are Algorithms that Suggest Various FUE Densities and Hair Mass Measurements for Removing Grafts, but the Surgeon can Change the Algorithm Upward or Downward to Create Greater or Lesser Residual Densities or Hair Mass Measurements in the Donor Area as the Grafts are Removed. In addition, although the Computer System will Suggest Optimum Spacing for the Extracted Follicles to Minimize Confluence of Missing Follicular Units, the Surgeon can Override this Feature

A

Figure 2

A

Once the Headgear is Positioned and the Computer Assessment of the Donor Area is Complete, the Surgeon Brings his Attention to Implanting the Grafts in the Recipient Area. He can Request Single, Two Hair, Three Hair or Even Large Number of Hairs Per Grafts, One Grafts at a Time. Assuming that he Wants to Start by Creating the Leading Edge of the Hairline, he may Request Single Hair Grafts One at a Time, a Robot at the Back of the Head will Identify the Area which the Surgeon Prioritized and Start Removing, with a Special Punch, the Requested Grafts. With each Graft Excision, the Graft will be Transported by Tubing from the Donor Area to the Hand-held Duplex Implanter. Along the Path of Transport an Optical Detector Inspects the Graft for Graft Integrity. This Process will take Less than One Second. The Graft will be Implanted by the Surgeon. This is an Iterative Process and the Surgeon will Identify the # of Hairs/graft of each Step of the FUE and the Implantation Process One at a Time The Surgeon may Allow the Computer to Select the Area for Excision based Upon Calculations of Residual Donor Densities in the Areas Chosen by the Surgeon The Surgeon may want to Control how the Robot Moves about the Donor Area, so this is an Option Available to the Surgeon At all Times, the Surgeon will be Able to Visualize, in Digital Graphic Format, the Residual Donor Density and the Residual Donor Hair Mass. The Surgeon Further can Visualize, via Data that Records the area of Abnormal Spacing created by the Extraction Process, the Degree of 'Patchiness' Created by the FUE Process. Visualization is selectable by Local Area or Globally Implantation can be Performed with a Hand-held Implanter. As the Recipient Area Fills in, Donor Depletion of the Donor Area will be Shown to the Surgeon Implantation can be Performed by a Robot, Using a Plan Created Prior to the Surgery. This Plan will Define, in Advance Graphically, the Location where Grafts of Various Sizes can be Implanted

Figure 2 (Continued)

Manual Duplex

A

B

C

CHOI-Style Duplex

Comparison

CHOI-Style Duplex

Duplex Manual

| LEFT | Patient 007 | Right |
|---|---|---|
| **Area 12** | **Reference Donor Area** | **Area 9** |
| 120,000 | Global Hair Count | 120,000 |
| 50,000 | Global Graft Count | 50,000 |
| 54 | Average Hair Thickness (Microns) | 54 |
| 28510 | Global Hair Mass (mm) | 28510 |
| 2.4 | Total Global Donor Density Hairs/mm2 | 2.4 |
| | **Activity Area** | |
| 62 | Hair Count | 38 |
| 23 | Follicular Unit Count | 18 |
| 2.7 | Donor Density in Active Field | 2.1 |
| 54.0 | Hair thickness in Microns | 54.0 |
| 142 | Hair Mass in Active Area Below (mm) | 87 |
| NA | % Reduction of Hair Mass Below (mm) | NA |

| LEFT | Patient #002 | Right |
|---|---|---|
| **Area 9** | **Reference Area** | **Area 9** |
| 100,000 | Global Hair Count | 100,000 |
| 50,000 | Global Graft Count | 50,000 |
| 54 | Average Hair Thickness (Microns) | 54 |
| 28510 | Global Hair Mass (mm) | 28510 |
| 2 | Total Global Donor Density Hairs/mm2 | 2 |
| | **Activity Area** | |
| 30 | Hair Count | 44 |
| 17 | Follicular Unit Count | 23 |
| 1.8 | Donor Density in Active Field | 1.9 |
| 54.0 | Hair thickness in Microns | 54.0 |
| 69 | Hair Mass in Active Area Below (mm) | 101 |
| 32% | % Reduction of Hair Mass Below (mm) | NA |

HAIR TRANSPLANTATION SURGERY WITH GRAFT-ON-DEMAND PROCESSING OF FOLLICULAR UNITS

CROSS-REFERENCE TO RELATED APPLICATIONS

This application claims benefit of priority from U.S. Provisional Application No. 63/516,264 filed Jul. 28, 2023, the content of which is incorporated by reference as if set forth herein in full.

BACKGROUND

1. Technical Field

The field generally relates to hair transplantation surgery, harvesting of follicular units from a donor region which is typically the scalp of a patient, and implantation of these follicular units into recipient regions of the scalp.

2. Discussion of Related Art

Conventionally, hair transplant surgery is a lengthy, tedious and labor-intensive procedure, roughly involving the steps of harvesting individual hair grafts, trimming the hair grafts, sorting the grafts, storing the grafts, preparation of the grafts for implantation, recording the number of hairs per graft, counting the damaged hair grafts and deciding how to manage them, and actual implantation of the grafts at recipient regions of the scalp.

In conventional hair transplant surgeries, to harvest grafts, the surgeon or a robotic device harvests individual hair grafts from a donor region of the scalp. Harvesting of grafts may proceed robotically, for example, U.S. Pat. No. 9,913,610, "Systems and methods for selecting a desired quantity of follicular units" by Restoration Robotics. The follicular units (grafts) are typically harvested using a procedure called follicular unit extraction (FUE) where individual follicular units are punch-harvested from the donor region and delivered to a hydration bath.

In conventional hair transplant surgeries, to prepare the grafts for implantation, a technician (typically a skilled surgical assistant) sorts the grafts depending on the number hairs included in the follicular unit (most commonly, one, two or three hairs, although higher numbers are sometimes seen). The technician discards fully damaged or decapitated hair grafts, trims partially damaged grafts, and then places the grafts in a storage medium. The hair grafts are stored in an organized way so that they can be retrieved easily and by the needed number of hairs in the graft, and are kept viable while awaiting implantation. As needed, the grafts are loaded by the technician into an implantation handpiece ready for implantation by the surgeon directly through the scalp with a sharp implanter, or if premade sites are made by the surgeon, then implantation can be performed by a technician using a dull implanter.

In conventional hair transplant surgeries, preparation of the grafts in particular involves sorting the numbers of hairs per graft yielded, discarding decapitated hair graft, trimming partially damaged hair grafts, placing these hair grafts into a solution, storing these hair graft in a solution in an organized way so that they can be retrieved easily, and that will keep the graft viable while awaiting implantation, and loading the grafts into an implantation handpiece ready for implantation.

In actual implantation, for each area in the recipient region of the scalp, the surgeon determines the nature and characteristics of the desired graft (for example, the number of hairs needed for that particular location), makes (or pre-makes) an incision into the scalp and (using the loaded implantation handpiece) implants a suitable graft into the recipient region. The same implantation process can be performed using jeweler's forceps instead of an implantation handpiece by a technician if incisions have been pre-made at the recipient site.

Today's commercial implantation procedures are often operated by one surgeon and teams of technicians. Alternatively, surgical assistants can use jeweler's forceps to handle and possibly place the graft. It is not unusual as grafts are handled by many people that damage to the hairs in the graft can be fatal to individual hairs within the graft or all of the hairs within the graft. Damage can occur from rough handling of the grafts or by allowing the grafts to dry by exposing the grafts to air for more than 20 seconds. Today's FUE requires highly skilled technicians who understand quality control in handling hundreds or thousands of grafts. It is not unusual for larger FUE hair transplant session, to deploy 5-8 technicians dedicated to the handling and movement of grafts from the donor site through the sorting process, into the storage media and finally into the recipient area for implantation.

Given that a typical procedure involves between 1000-5000 individual grafts, a typical surgery might last between 6-12 hours for completion. As more grafts are harvested, more technicians are often needed.

SUMMARY

In conventional procedures, the first two of these steps, i.e., harvesting and preparation of grafts, are repetitive steps that, although time-consuming, are tedious, fraught with human problems technologically, such as hand or eye fatigue which often impact the quality of the grafts. Moreover, the long-term consequences of FUE harvesting can produce a variety of hand and eye disabilities for the staff and the surgeon.

It is the third of these steps, implantation, that differentiates surgeons who are technically skilled and competent from those who are also artists. It is easy to stretch the analogy too far, but in a sense as applied to hair transplant surgery, the recipient region of the scalp is the surgeon's canvas and the implantation handpiece is their brush. The surgeon-as-an-artist develops a mental picture of the finished surgery, and instantiates this vision by painstaking steps in which the surgeon selects a specific implantation site, selects a follicular unit with the desired number of hairs for implantation into the selected implantation site, and makes the implantation to desired depth, width and angle which determine the distribution and the direction of growth of the hair(s) in each graft.

The surgeon-as-an-artist must also consider graft depletion from the donor region during graft harvesting. The surgeon estimates the number of grafts he/she needs to fill in the patient's recipient area. Then the surgeon harvests this number of grafts he/she determine will meet the needs of the patient's recipient area. The donor area that is harvested with the FUE harvesting technique, reflects between 20-25% of the total surface area of the scalp, is located in a 3-inch-high band of scalp around the side and back of the head and has a finite number of grafts in this area. The distance between grafts, normally averages about 1 mm per graft in an irregular pattern. Generally, a typical male will have between 10,000-12,000 follicular units in the 20-25% area around the sides and back of the head (donor region). Individual hairs contain mass that the surgeon classifies the hairs as fine hair (25-40 microns), medium hair (40-60 microns) or coarse hair (greater than 60 microns). Clearly overlap occurs despite the ability to measure hair shaft thickness in the donor area. A coarse-haired individual may have more than 6 times the hair mass per hair as compared to an individual with very-fine hairs. Also, each graft contains between 1-3 hairs on average. The surgeon must be aware of all of these quantitative elements when he/she determines how many grafts are removed. In this regard, as hair graft are removed from the donor area, donor depletion starts occurring immediately after the first FUE is performed (insignificant on the first set of excisions). The more grafts that are removed, the greater will be the depletion of the donor hair supply. At some point, too many grafts may be removed creating a see-through appearance in the donor area or even frank balding of the donor area. Everyone has a limit as to how many grafts can safely be removed. People with more hair per graft, who contain a coarser hair greater than 60 microns (possibly 80 microns) and/or who have a hair color which more closely matches the skin color (e.g., white hair against white skin), can have the most grafts removed with FUE. People who have very fine thread-like hair, a low hair count per graft and who have a high contrast color between hair and skin (e.g., black hair on white skin), will have a significantly limited donor supply. The donor area's capacity can be safely harvested through calculations based upon standard known formulae for original hair densities, residual hair densities, total donor hair mass, residual donor hair mass. In addition, although the grafts are randomly located in the scalp, they average 1 graft per square mm throughout the entire donor area. As these grafts are removed, spaces develop that reflect the removal of grafts such that the uniform randomness of the non-harvested donor area is replaced after FUE with a patchy distribution of the residual grafts. The surgeon's eye must control the degree of this new patchiness so that it is not apparent in the patient after the surgery is complete.

With respect to the donor region, it should be understood that the donor region is not limited to the scalp of the patient. The description herein focuses on the scalp because most hair transplant are done in the scalp; however, more and more a donor region in the beard is used because the beard hair is coarse and grows out long, almost as long as scalp hair. Pubic hair has also been used because it is coarse. Surgeons are now taking hair from every part of the body. Thus, although the description herein focuses on scalp hair for the donor region, it will be understood, that the scalp is not the only donor area in the human body.

The surgeon's progress through the surgery is often hindered and slowed by the time needed for harvesting and preparation of the grafts, thus slowing the pace at which the surgeon's mental picture of the harvested donor area is realized.

Embodiments of the instant disclosure involves a graft-on-demand system in which grafts are harvested robotically based on current needs of the surgeon and delivered directly into an implantation handpiece, virtually eliminating the need for graft handling, intermediate storage, preparation of the graft for implantation and implantation. According to this aspect, the system uses machine vision to survey the donor region of the scalp, beard or other body parts to map the location of each candidate follicular unit, including the number of hairs in each candidate unit. During surgery, the surgeon issues commands to the controller requesting grafts containing a specific numbers of hairs and/or other specific characteristics of the graft as desired by the surgeon for implantation at his chosen implantation site. Using robotics and by reference to the map of the donor region, the system punch-harvests a suitable follicular unit matching the surgeon's request and delivers the follicular unit via tubing directly into the implantation handpiece, bypassing the traditional hydration bath, all human handling and other preparatory steps. As the grafts are moved from the point of excision through the tubing to the point of implantation, the grafts will be passed through an optical detector, to determine and document any damage to the graft from the point of excision. If, for any reason, a graft is removed and has a significant number of transected hairs, the surgeon will be instantly notified of the graft status and given the choice to discharge the graft before implantation. The surgeon then implants the graft to the recipient region directly through the intact scalp skin of the recipient area using a very sharp needle (percutaneous implantation) or through a premade incision using a dull needle. The expected time from issuing the request to implantation of the graft should be between 1-2 seconds, which results in a significant reduction in the overall procedure time, possibly down to around 1-2 or 2-3 hours for the entire surgery. If more than one robotic arm is used, the speed of harvesting can increase with a proportionate reduction of the surgical time.

In some embodiments, the robot will have rotational abilities to move in an arc of 360 degrees. The purpose of such flexibility is to be able to reach other body donor area such as the beard under the chin, and the arms, legs, chest, abdomen and pubic areas.

A special punch is used in conjunction with suction through the punch that can completely excise the graft from the patient's donor area and allow the graft to be immediately transported to a handheld implanter held by the surgeon. As one example, a trumpet punch with an eccentric sharp cutting edge connected to suction, causes a slight lateral vibration during excision of the graft, and tends to completely excise grafts without damage more than 90% of the time, allowing simple suctioning of the graft to the implantation handpiece, and the residual 10% of the time grafts are easily detached from their base ends by suction close constantly applied by the harvesting instrument.

The command to harvest a follicular unit with the designated characteristic (such as number of hairs) may be issued by various means such as by voice command, by operation of a foot pedal, by one or more buttons on the implantation handpiece, and so forth and possibly in combinations.

Beneficial effects of embodiments described herein include the greatly shortened time needed for transplantation surgery, thereby allowing the surgeon-as-an-artist to fulfill the mental picture of the finished surgery without the hindrances imposed by traditional harvesting and preparation of graft. In addition, handling of the graft, which is a major source of graft damage, is essentially eliminated, as is the time that the graft remains out of the body and is susceptible to deterioration or graft death.

According to further aspects described herein, during surgery, the system monitors depletion of the donor site and provides real-time feedback to the surgeon, thereby allowing the surgeon to avoid over-depletion of the donor site. Appropriate computer algorithms will determine all of the mathematical variables at the onset of the surgery and monitor the changes in hair mass and uneven graft distribution in real-time. The surgeon can make judgments during graft excision based upon the real-time information supplied to him/her as the surgery progresses. In another embodiment, computer software and/or artificial intelligence can be used to balance a more uniform residual graft spacing in the donor area.

According to further aspects described herein, the harvested grafts are transported past an inspection station between the extraction device and the implantation handpiece. For this purpose, an inspection camera is provided at the inspection station and the tubing through which the harvested graft is transported by suction to the implantation handpiece is transparent or partially cut away at the inspection station. The harvested graft is imaged as it is suctioned past the inspection station, and using machine vision a determination is made to distinguish between grafts of acceptably high quality and those of poor quality, so that grafts of poor quality can be discharged without implantation at the recipient region.

According to further aspects described herein, a tensioning belt may be applied in the vicinity of the donor region of the scalp for stabilizing the head of the patient against a head rest. The tensioning belt may further be constructed to facilitate mapping of the donor region and graft excision. In this aspect, the tensioning belt has tines on the underside to correspond to the length of the donor area, has elastic appendages containing hook-like needles that hang from the inferior side of the tensioning belt producing traction on the scalp below it, reducing scalp laxity below the tensioning belt, allowing for easier FUE. Fiducial marks may be provided on the traction belt to allow the donor region to be mapped with accuracy along with lines drawn by the surgeon on the scalp with an indelible pen surrounding the donor area prior to the application of the tensioning belt. Reduction in scalp laxity provides for improved harvesting of follicular units (grafts). This same belt can be used to stabilize the head as part of additional hardware designed to minimize the patient's head movement during the surgery.

According to further aspects described herein, a head stabilization apparatus may be provided to fix the position of the patient's head during the transplantation procedure. In this aspect, the head stabilization apparatus includes a chest rest, and a semicircular headrest supported by a pair of arms which extend upwardly from the chest rest. The lengths of the arms are adjustable such as by locking telescopic arms. A fixation strap is adjustably attached to opposite ends of the headrest for fixation of the head of a patient against the headrest, wherein the fixation strap is attached to the headrest with a quick release mechanism such as Velcro pads.

According to further aspects described herein, a thumbtack fiducial may be provided for fixation to skin at a donor region of a patient. In this aspect, the fiducial includes a plate having an upper surface and a lower surface, with a pair of needle-like legs extending downwardly from the lower surface of the plate. The needle-like legs are biased outwardly so that they spread outwardly as the fiducial is inserted into the skin. A slidable retainer ring encircles the legs and is slidably positionable at a first position before insertion of the fiducial into the skin where the legs are retained in a vertical orientation against the outward bias of the legs, and at a second position as the fiducial is inserted into the skin where the retainer ring slides upwardly allowing the legs to extend outwardly underneath the surface of the skin. Another embodiment for the thumbtack fiducial could be a spring-loaded fishhook type retractable structure. A fiducial mark is formed on the upper surface of the plate. In certain embodiments, the plate is comprised of a circular disk of approximately 5 mm diameter, and the fiducial may be provided as part of a sterilizable kit comprising plural ones of the fiducials and the fixation strap for the head stabilization mechanism.

According to further aspects described herein, an apparatus for harvesting hair grafts from a donor region includes a controller configured with machine vision to map follicular units at the donor region; one or more robotic arms controllable by the controller in angular and translation movement in x/y/z directions relative to the donor region; and punch harvesting instruments mounted to one or more robotic arms, wherein the punch harvesting instrument is configured to harvest follicular units from the donor region by movement of the robotic arm(s) and under control of the controller. The controller is further configured to accept a command to harvest a follicular unit with a designated characteristic such as number of hairs, and to operate the robotic arm and the punch harvesting instrument to harvest such follicular units by reference to the map of follicular units. The harvested follicular unit is delivered by tubing to an implantation handpiece via suction.

The controller may be further configured to monitor depletion of hair grafts from the donor region, and further comprising a graphical display, to display a visual and/or statistical depiction of the depletion of hair grafts from the donor region in real time.

The controller may be further configured to monitor the spacing from graft removal in the donor area, and further comprising a graphical display, to display a visual and/or statistical depiction of the ideal spacing between grafts resulting from the removal of hair grafts from the donor region in real time.

A source of saline (or similar biological fluid) may be provided, to introduce saline to the tubing in the vicinity of the punch harvesting instrument to enhance the effect of suction and/or to facilitate delivery of the harvested follicular unit to the implantation handpiece.

According to further aspects described herein, saline solution is introduced at key points into the delivery system for delivering the harvested graft from the donor region to the implantation handpiece. By introducing the saline at these key points, the graft is lubricated as it travels in the delivery system, thereby helping to reduce resistance to the graft and to reduce the possibility of clogging of the tubing by the graft, while at the same time increasing the effectiveness of vacuum for complete excision of the graft from the donor region and the effectiveness of aspiration of the graft to the implantation handpiece.

According to further aspects described herein, a movable tensioning pad may be provided, for movement in coordination with movement of the harvesting instrument, so as to tension the scalp in the vicinity of the donor region while harvesting the follicular unit. The tensioning pad may be mounted on an auxiliary robotic arm for the tensioning pad, for its coordinated movement. In other embodiments, the tensioning pad may be mounted by a flexible arm connected to the harvesting instrument or the robotic arm, for movement in coordination with movement of the robotic arm and the harvesting instrument.

According to further aspects described herein, an implantation handpiece includes a generally cylindrical body for gripping by a user of the implantation handpiece; first and second channels positioned on the cylindrical body, wherein the first channel is connectable to a source of vacuum and the second channel is connectable to a source of harvested follicular units; and a central rod and a hollow needle, wherein the central rod and the hollow needle are positioned for slidable and relative movement of the rod inside the needle. In a retracted position of the rod relative to the needle, a harvested follicular unit is delivered from the second channel to an interior of the hollow needle under force of vacuum applied to the first channel at a position forward of the central rod. In an implantation position, a slidable movement of the central rod relative to the hollow needle drives the follicular unit from the hollow needle into an implantation site.

A third channel may be provided for controllable introduction of pressure under control of the user, wherein introduction of pressure from the third channel drives the central rod from the retracted position to the implantation position.

A third channel may be provided for controllable introduction of vacuum, diverted from source, to drive the follicular unit from the hollow needle into an implantation site.

In some embodiments, in the retracted position the central rod is fit loosely inside the hollow needle, the first channel is positioned at a rearward side of a forward end of the central rod and the second channel is positioned at forward side of the forward end of the central rod, and the fit of the central rod inside the hollow needle is sufficiently loose as to allow vacuum applied from the first channel to reach alongside the central rod and to suction a harvested follicular unit from the second channel.

Also in some embodiments, slidable movement of the central rod relative to the hollow needle is effectuated manually be the user.

According to further aspects described herein, a tensioning belt for application to a donor region of a scalp includes a flexible band of suitable length to wrap around the head of the patient at frontwise position slightly above the patient's eyebrows to a rearwise position at the most inferior area of the crown of the patient's scalp. Plural fiducial marks may be fixed to the band by which specific follicular units in the donor region are reproducibly locatable, and plural tines extend from the underside of the band for anchoring into an upper region of the scalp, above the crown. Plural elastic cords may extend from the band, each such elastic cord terminating in a hook, wherein the hooks are constructed to punch into the high scalp below the band and above the donor region to produce traction on the donor region of the scalp and to reduce scalp laxity.

According to further aspects described herein, depletion of hair grafts from a donor region of a patient's scalp during transplant surgery is monitored by imaging the donor region of the scalp, such as with a vision system, wherein the donor region being divided into a plurality of zones, and by storing initial statistical content of candidate grafts in each of the plural zones, wherein the initial statistical content is collected automatically at a time prior to commencement of transplant surgery and includes candidate density and hair mass measurements in each such zone. Ongoing statistical content of candidate grafts in each of the plural zones is gathered, wherein the ongoing statistical content is collected automatically at a time during harvesting of grafts from the donor region during transplant surgery and includes current candidate density and hair mass in each such zone. A visual depiction is displayed to the surgeon for comparing the initial statistical content and the ongoing statistical content for one of more zones of the donor region in real time during transplant surgery.

In one embodiment, a marker of known width will be placed on the patient's harvesting area during the initial photo-documentation of the harvesting area. This marker will be a small rectangle possibly measuring 1000 microns by 50 microns. Cameras will reference this marker to determine hair shaft thickness throughout the donor area, a crucial measurement for determining the hair mass of multiple single hairs within grafts and the residual hair mass of the donor area as hair depletion is occurring in real time.

In some aspects, the marker may form a fiducial constructed for fixation to skin at a donor region of a patient, wherein the fiducial includes a plate having an upper surface and a lower surface, an appendage extending downwardly from the lower surface of the plate, wherein the appendage includes an embeddable segment constructed for insertion into the skin, an anchor positioned along the embeddable segment of the appendage for anchoring the appendage in the skin, a fiducial mark formed on the upper surface of the plate, and a release mechanism that allows the fiducial to be easily removed from its imbedded position in the scalp. The embeddable segment of the appendage has a length so as to extend approximately 1.5 mm beneath the skin when the fiducial is fixed to the skin. The plate may have an area or around 20 square-mm such as a circular disk of approximately 5 mm diameter.

In some embodiments, the appendage may take the form of a pair of needle-like legs extending downwardly from the lower surface of the plate, wherein the needle-like legs are biased outwardly so that they spread outwardly as the fiducial is inserted into the skin, together with a slidable retainer ring which encircles the legs and is slidably positionable at a first position before insertion of the fiducial into the skin where the legs are retained in a vertical orientation against the outward bias of the legs, and at a second position as the fiducial is inserted into the skin where the retainer ring slides upwardly allowing the legs to extend outwardly underneath the surface of the skin. Anchoring of the appendage is accomplished by the outwardly extending legs underneath the surface of the skin.

In other embodiments, the appendage may include a compression spring positioned beneath the lower surface of the plate and constructed for abutment against the surface of the skin, and the anchor may be formed by a hook positioned along the embeddable segment below the compression spring.

In some embodiments, the display may further include the display of current images of zones of the donor region in comparison with initial images of zones of the donor region. In addition, on images of zones of the donor region, the display may further superimpose information designating characteristics of each candidate, the characteristic information including at least the number of hairs or follicular units in each candidate.

Embodiments contemplated herein include any and all of methods, systems, apparatus, tangible computer-readable media and others, related to the description provided herein.

Further objectives and advantages will become apparent from a consideration of the descriptions, drawings, and examples.

BRIEF DESCRIPTION OF THE DRAWINGS

FIG. 1A is a diagram depicting aspects of an on-demand harvesting system according to the disclosure herein, in which the surgeon manipulates the implantation handpiece by hand.

FIG. 1A-1 is a magnified view of an inspection station of FIG. 1A, showing a cut-away view of a tube that transports a harvested graft by suction from a donor region toward an implantation handpiece.

FIG. 1B-1 is a magnified view of an inspection station of FIG. 1B, showing a cut-away view of a tube that transports a harvested graft by suction from a donor region toward an implantation handpiece.

FIG. 2 is a flowchart depicting typical steps in an on-demand hair transplantation procedure.

FIGS. 7B-1 through 7B-5 illustrate a scalp tensioning pad mounted to a tensioning robotic arm for independent and coordinated movement of the scalp tensioning pad in coordination with movement of the robotic arm for the harvesting instrument.

FIGS. 7C-1 through 7C-6 illustrate a scalp tensioning pad mounted by a flexible arm to the robotic arm for the harvesting instrument for movement in coordination with movement of the robotic arm.

DETAILED DESCRIPTION

Embodiments falling within the disclosure herein include aspects concerning a system for on-demand harvesting of follicular units and delivery of the harvested follicular units to an implantation handpiece, optical inspection of the quality of extracted grafts, implantation handpieces adapted to receive harvested follicular units, a tensioning belt to stabilize the patient's head such as against a headrest and/or to produce traction on the donor region of the scalp and to reduce scalp laxity, use of a tensioning pad adjacent to the extraction device to produce locally increased tension on the scalp, depletion monitoring of the donor region of the scalp, saline infusion to delivery tubing which improves aspiration of harvested follicular units to the implantation handpiece, and so forth.

On-Demand Harvesting System

Figures 1, 1A:
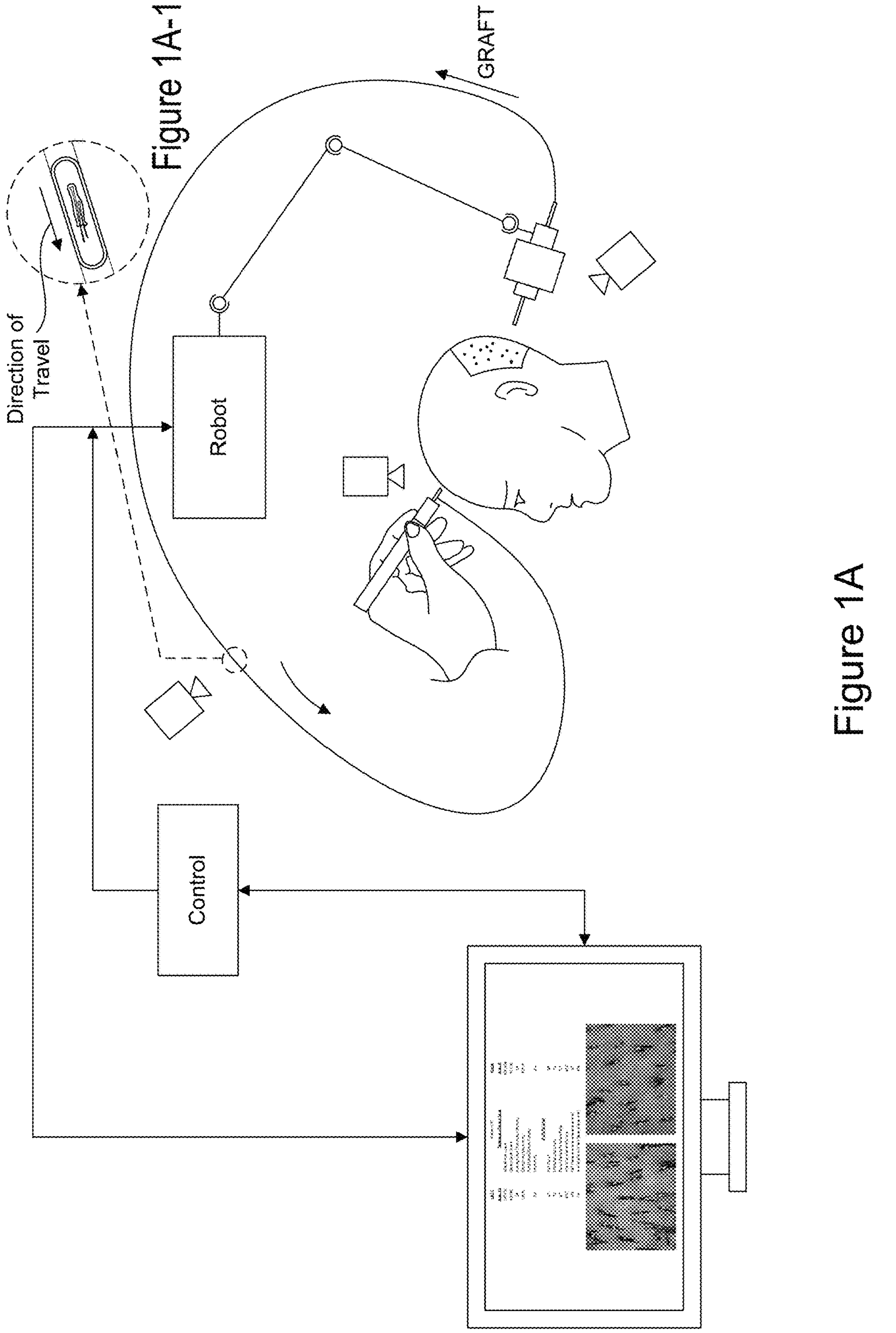

FIG. 1A is a diagram depicting aspects of an on-demand harvesting system according to the disclosure herein, in which the surgeon manipulates the implantation handpiece by hand.

Briefly, as shown in FIG. 1A, an apparatus for harvesting hair grafts from a donor region includes a controller configured with machine vision to map follicular units at the donor region; one or more robotic arms controllable by the controller in angular and translation movement in x/y/z directions relative to the donor region; and a punch harvesting instrument mounted to each robotic arm, wherein the punch harvesting instrument is configured to harvest follicular units from the donor region by movement of the robotic arm and under control of the controller. The controller is further configured to accept a command to harvest a follicular unit with a designated characteristic such as number of hairs, and to operate the robotic arm(s) and the punch harvesting instrument(s) to harvest such a follicular unit by reference to the map of follicular units. The harvested follicular unit is delivered by tubing to an implantation handpiece via suction.

The controller is further configured to monitor depletion of hair grafts from the donor region, and further comprising a display to display a visual depiction of the depletion of hair grafts from the donor region in real time.

A source of saline may be provided, to introduce saline to the tubing in the vicinity of the punch harvesting instrument to enhance the effect of suction such as for improved detachment of the graft from the skin and/or to facilitate delivery of the harvested follicular unit to the implantation handpiece.

In more detail, a patient whose scalp includes a donor region and a recipient region is seated with head immobilized for the duration of the transplantation procedure. Preferably the patient may be sedated, or is distracted/entertained during the procedure such as by use of artificial reality googles.

A robotic arm(s) with multiple axes, is positioned adjacent the donor region and is configured for movement in translation and angle in x/y/z directions. A punch harvesting instrument is mounted to the arm and is connected to a vacuum source so that when the graft is excised, it instantly travels from the punch, through tubing and directly into an implanter. The use of suction also enhances graft removal. Preferably, the punch harvesting instrument is tipped with an excision needle for hair grafts with a possible "Trumpet" shaped punch is aligned in the direction of the hair using optical sensors, wherein the cutting surface of the punch points away from the axis of the center of the excision needle. In some embodiments the harvesting instrument causes the punch to rotate or vibrate or oscillate, or otherwise to move, so as to improve the ability of the punch to penetrate the tough outer dermal layer and then to descend through the subdermal layers to the desired excision depth, while decreasing the chance of damaging the graft (for example, damage caused by transecting the graft). The Trumpet design may be replaced with a more standardized drill bit. One or more small cameras may be mounted on the robotic arm to guide the punch into the proper position for extraction of the graft. Cameras may be mounted in close proximity to the punch, or they can be mounted further away from the proximity of the punch and thereby to provide triangulation views to guide the punch into the exact position and the ideal angle for the removal of the graft.

The harvesting instrument and the robotic arm are operated under control of a controller. A camera is positioned for imaging of the donor region, which is imaged in both in a pre-surgery mapping and survey phase as well as during the course of the surgery.

More particularly, during a pre-surgery mapping and survey phase, the controller obtains imagery from camera(s)

which are used by the controller to create a map of the donor region. The map of the donor region includes information about targeted grafts for follicular unit harvesting, the information including the distribution of candidate grafts in the donor region, the location of each candidate, as well as characteristics of the candidate such as number of hairs in each candidate. The controller creates the map using machine vision technology which may also involve a trained neural network or other form of artificial intelligence to establish pattern recognition imprints of a map of the donor area. Fiducials may be placed directly onto or into the scalp in various positions for purposes of reference, and fiducials may likewise be positioned on a tensioning belt as described below in connection with FIG. 7A.

During the course of the surgery, the controller refers to the map so as to reposition the harvesting instrument over a candidate having characteristics (such as number of hairs) that match to a request issued by the surgeon. The controller thereafter activates the harvesting instrument to harvest the follicular unit, which is delivered by tubing directly to the implantation handpiece, for implantation by the surgeon into the recipient region of the scalp.

Although this embodiment includes a pre-surgery mapping and survey phase, the location and other information on candidates for graft excisions may also be obtained during actual surgery, which tends to compensate for and allow movement of the patient's head during the procedure. Pattern recognition technology or the use of fiducials will assist in this process to ensure that the expected position of the graft targeted for excision matches to the actual position of the targeted graft, despite movement and repositionings of the donor region.

The surgeon must have a plan as he/she embarks on the hair transplant. The number of grafts required, an essential part of the plan, can be input into the System's software. As the entire donor area is mapped, the projected distribution of FUE grafts can be calculated by the system's computer, in such a way, to distribute the extractions uniformly across the donor area so that the hair mass of the donor area is uniformly maintained in its appearance. At the onset, the controller will display the total number of one, two and three hair grafts in the donor area so that the surgeon can make judgments as to which number of hairs per graft he might want to use throughout the surgery. In donor areas where there is more hair mass, for example, more extractions will occur as these areas can handle a greater reduction of hair mass than other areas with less hair mass. The distribution of extractions based upon hair mass will avoid imbalances in graft depletion in any single part of the donor area.

As further depicted in FIG. 1A, sources of pressure and/or vacuum are provided, and all of the harvesting instrument, the implantation handpiece, and the sources of pressure and/or vacuum, as appropriate, are interconnected by tubing so as to effectuate the delivery of the harvested follicular unit directly to the implantation handpiece, under request from the surgeon, without any significant intermediate storage or other preparation of the graft prior to implantation.

During the course of the surgery, the controller also monitors the depletion of hairs in variously defined donor regions and the residual hair mass of such defined donor regions. A real-time display of depletion is provided to the surgeon on the display depicted in FIG. 1A and as explained in greater detail below in connection with FIG. 8A.

During the course of the surgery, hair grafts are extracted from a donor area by controllable positioning of a hair excision instrument for removing follicular units (grafts) containing specifically from 1-3 or more hairs, on demand by the surgeon. One or more cameras are mounted on the end of the robotic arm(s) or at a specified distance from the donor excision field to align the hair excision instrument with the direction of the hairs in the graft (adjusted to a bend of the hairs in the graft at its exit point chosen for excision as demonstrated in U.S. Pat. No. 6,572,625, "Hair transplant harvesting device and method for its use". These grafts are moved directly from the excision instrument via suction and tubing, past an optical inspection station, to an implanter to allow the surgeon to rapidly place the grafts into the balding area with almost no out-of-body time.

In accordance with aspects of the disclosure herein, a hollow instrument with a cutting edge such as a hollow drill or "Trumpet" punch with a diameter between 0.7-1.1 mm, roughly the width of a follicular unit is used to cut into the scalp. The selection of which grafts are to be removed is the result of (1) the decision of the surgeon to address the needs of the recipient area, (2) the impact of the graft removal based upon minimizing the voids and uneven distribution of the remaining grafts left behind after each excision, (3) the impact of donor mass depletion of hairs and/or hair mass as the FUE progresses during the surgery, (4) an automated algorithm driven by formulae which ensure that graft removal is evenly distributed across the donor region in proportion to the density and spacing of candidate grafts in each zone of the donor region, (5) the use of an imaging system and depletion monitoring which allow the health care professional to over-ride the automated selection of a graft. The grafts are transported by suction through tubing, past an optical detection for automated inspection of the quality of the grafts, then into a handheld implanter, thereby allowing the surgeon to easily implant the grafts into the recipient area. As the wounds are very small, this results in relatively fast healing, minimal bleeding and virtually no grossly or minimally visible scar upon healing.

In some embodiments, the harvested grafts are transported past an inspection station between the extraction device and the implantation handpiece. For this purpose, an inspection camera is provided at the inspection station and the tubing that carries the harvested graft is transparent or partially cut away at the inspection station. The inspection station is shown in greater detail in FIG. 1A-1.

FIG. 1A-1 is a magnified view of an inspection station of FIG. 1A, showing a cut-away view of a tube that transports a harvested graft by suction from a donor region toward an implantation handpiece. The controller images the harvested graft as it is suctioned past the inspection station, to determine whether the graft is of viable good quality, or whether the graft has significant issues that might interfere with viability. Such issues include significant transections of the graft or amputation of some or all of the hairs in the grafts. Upon detection of a graft of poor quality, the controller provides a notification to the surgeon, such as an audible alert, so that the graft is not implanted. The surgeon, holding the handpiece, will have the option to discharge grafts of poor quality, keeping them out of the recipient area.

To distinguish between grafts of acceptably high quality and those of poor quality, the controller in some embodiments relies on machine vision such as a trained neural network. An image of the graft as captured by the inspection camera is provided to an input layer of a multilayer neural network such as a convolutional neural network. The neural network provides a classification output from the input of the image of the graft, signifying whether the graft is of acceptably high quality or is of poor quality. The neural network is trained on labelled data using methods known to those of ordinary skill, such as gradient descent, resilient backpropagation, conjugate gradient, quasi-Newton, Levenberg-Marquardt, abnormality detection, novelty detection and so forth. The labelled data by which the network is trained matches the input characteristics expected during operation, i.e., matches a population of a wide variety of grafts presenting with different modalities and number of hairs, where the majority of grafts are healthy and unacceptable grafts are uncommon.

In accordance with another embodiment an x/y/z stabilization gantry is employed to fix the robotic arms and the hollow instrument and thus the imaging system. In still another embodiment a suction device is positioned to create traction upon the graft to facilitate the cutting of a follicular unit and its removal from the donor area.

By virtue of arrangements within the scope of this disclosure, a so-called graft Robotic Assisted Loop System is obtained. This provides a "No-Touch" technique where the graft is excised (Follicular Unit) from the back of the head and then immediately transported to an implanter which is ready to place the graft into the recipient area. Among the benefits of such a system:

- Elimination of humans handling the grafts (major cause of graft damage)
- Elimination of graft storage (possibly reduce the shock of the hair transplant which occurs in close to 100% of patients today).
- Reduction in the size of the labor force for a surgery used for handling the thousands of graft in today surgery, to handling a minimal number of grafts.
- Reduction in the surgical time by eliminating multiple steps in today's procedure thereby reducing anesthetic time.

As a result, the system depicted in FIG. 1A, using a punch harvester such as a trumpet-tipped instrument, and using computer software which can identify a graft with the number of hairs required (graft on demand), is effective to drill down to the full depth of the graft while it is still in the back of the head. The implantation handpiece has a suction which facilitates the complete excision of the graft by utilizing suction in the excision phase of the FUE process through appropriate tubing to deliver it directly to the implantation handpiece. At the request/instruction/command of the surgeon to the controller and to the robotic software, on the desired characteristics of the graft (such as how many hairs per graft the surgeon wants), the implantation instrument, which is in the surgeon's hand, can then implant the graft percutaneously or in premade sites once the graft is delivered to the implanter. This beneficially allows the surgeon to simply communicate the number of hairs per graft and the computer software finds the graft with the number of hairs needed, gives the surgeon the option to select that particular graft or to advance to another graft. When the surgeon is satisfied with the identified graft, the punch on the robotic arm takes out the appropriate graft.

The command to harvest a follicular unit with the designated characteristic (such as number of hairs) may be issued by various means such as by voice command, by operation of a foot pedal, by one or more buttons on the implantation handpiece, and so forth and possibly in combinations.

Figures 1, 1B:
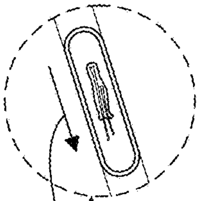
Figure 1B:
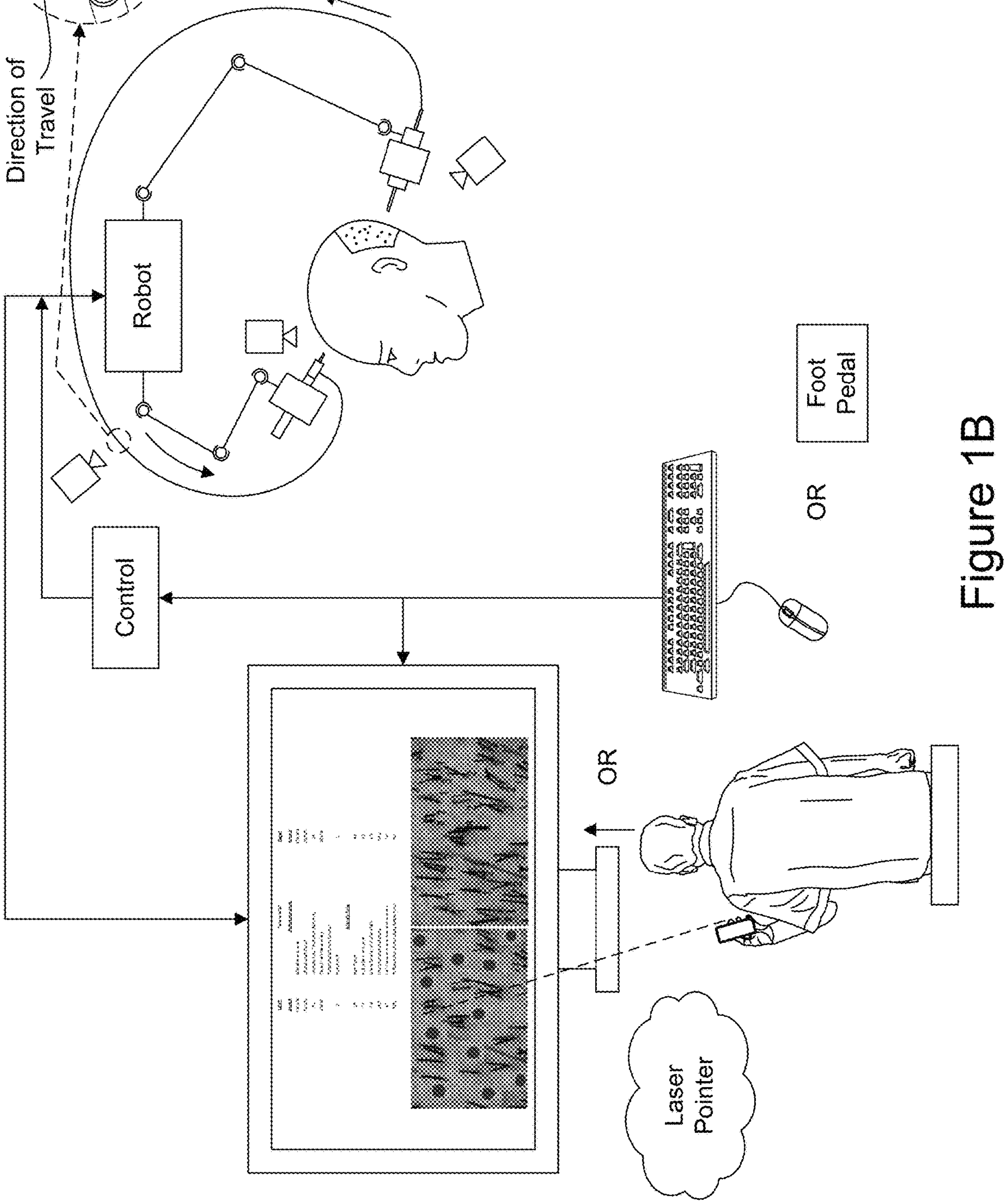
FIG. 1B is a diagram depicting aspects of an on-demand harvesting system according to the disclosure herein, in which the surgeon manipulates the implantation handpiece remotely, by robotic control.

FIG. 1B is a diagram depicting aspects of an on-demand harvesting system according to the disclosure herein, in which the surgeon manipulates the implantation handpiece remotely, by robotic control.

More particularly, although largely similar to the embodiment depicted in FIG. 1A, in one difference, in the embodiment depicted in FIG. 1B the surgeon manipulates the implantation handpiece remotely, by robotic control, whereas in the embodiment of FIG. 1A the surgeon manipulates the implantation handpiece by hand. A camera at the recipient/implant region provides the surgeon with a magnified view of the implantation region. The surgeon selects a particular implantation site and further selects implantation parameters such as implantation depth and angle. The surgeon issues a command for harvesting of a follicular unit with a designated characteristic such as number of hairs, and the controller operates the robotic arm(s) and the punch harvesting instrument(s) to harvest such a follicular unit. Similar to the embodiment of FIG. 1A, the harvested graft is delivered by suction to the implantation handpiece. Unlike the embodiment of FIG. 1A, in this embodiment the implantation handpiece is manipulated under control of the controller by a second set of robotic arms so as to implant the harvested graft at the implantation site selected by the surgeon and with the implantation parameters (such as implantation depth and angle) selected by the surgeon.

A real-time display of depletion is provided to the surgeon on the display depicted in FIG. 1B and as explained in greater detail below in connection with FIG. 8B.

Similar to the embodiment of FIG. 1A, the embodiment of FIG. 1B may also be provided with an inspection station and an inspection camera, whereby the controller distinguishes between grafts of acceptably high quality and those of poor quality, using machine vision.

FIG. 1B-1 is a magnified view of an inspection station of FIG. 1B, showing a cut-away view of a tube that transports a harvested graft by suction from a donor region toward an implantation handpiece. Upon detection of a graft of poor quality, the controller automatically discharges the graft once the graft reaches the implantation device, so that the graft is not implanted at the recipient area. A notification may also be provided to the surgeon, such as an audible alert.

Figure 7A:
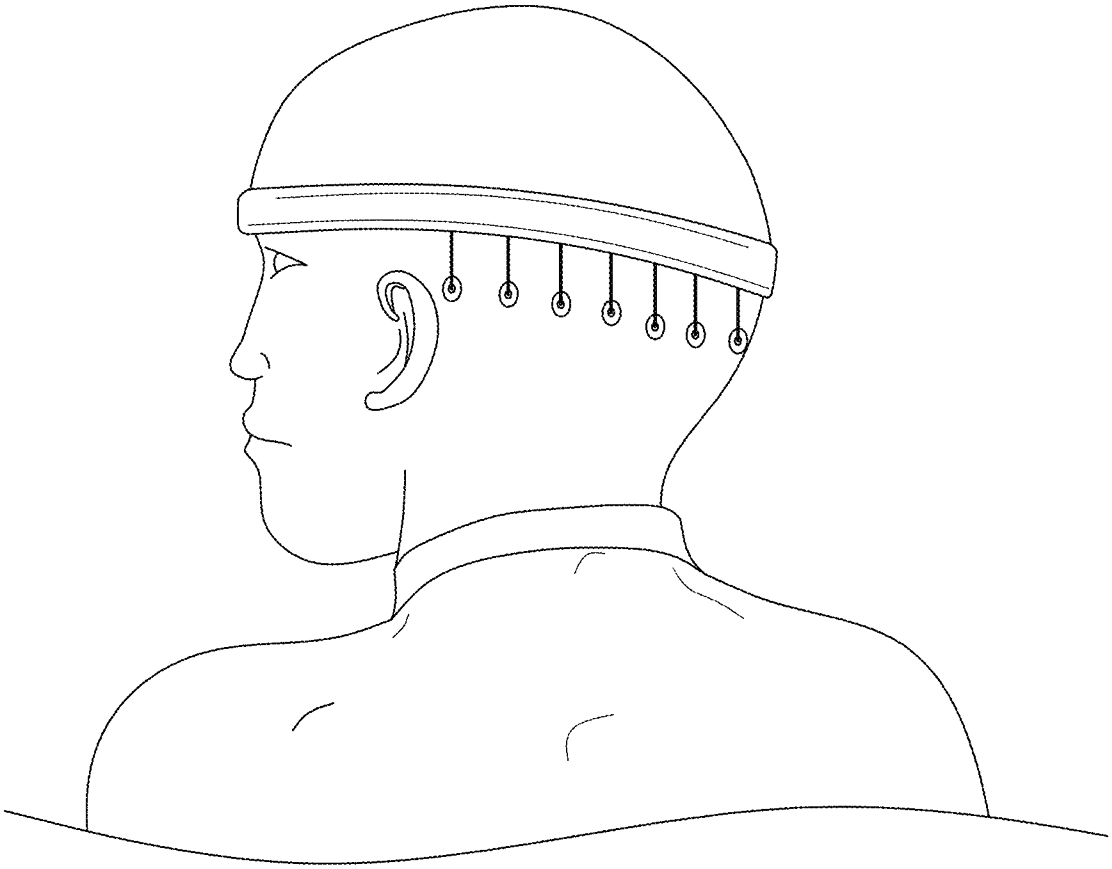
FIG. 7A illustrates a tensioning belt for application to a donor region of the scalp, so as to stabilize the patient's head such as against a headrest, and in this embodiment also being constructed with hooks so as to produce traction on the donor region of the scalp and to reduce scalp laxity.
Figures 1, 2, 3, 4, 5, 7B:
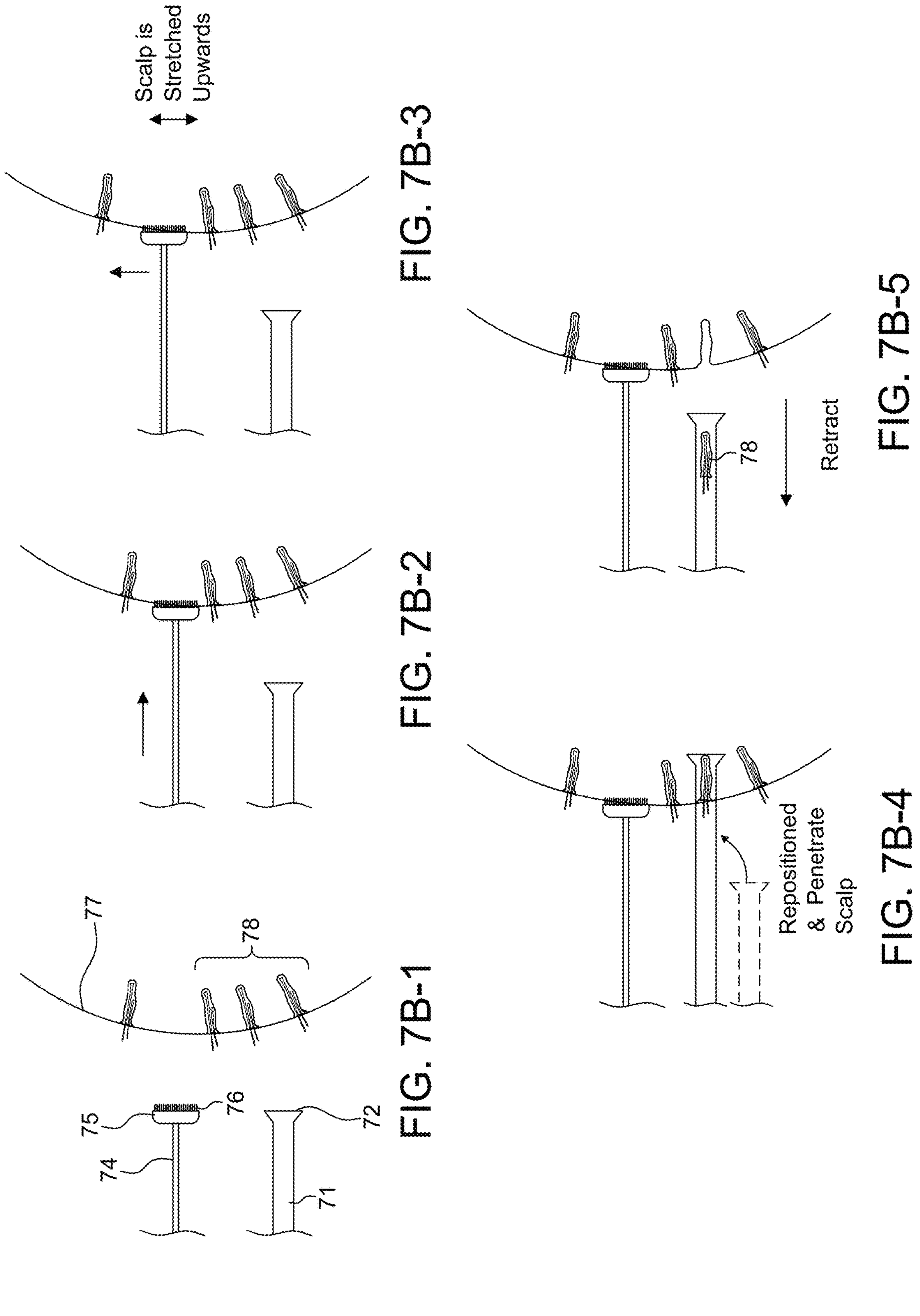

FIG. 2 is a flowchart depicting typical steps in an on-demand hair transplantation procedure.

As depicted in FIG. 2, the implantation procedure generally commences with the surgeon creating a hairline with patient. Prior to the beginning of the surgery, the patient and the surgeon meet to discuss the surgical plan, confirming his original estimate of the number of grafts required for the surgery, where they will be placed, and finally, if the hairline is involved in the planned surgery, draw a hairline on the patient's frontal area that reflects what the patient wants and what the surgeon believes is appropriate for the patient's outcome. The donor area is shaved and an outline of the area to be harvested is drawn with an indelible inked pen that will be recognized by the system's cameras. The donor area is subdivided into, for example, 10 zones with five vertical lines equidistant from each other and one horizontal line midway between the upper and lower border of the donor area.

Computer/camera assesses hair thickness, number of hairs, hairs-per-graft, distribution by area defined by surgeon. A complete picture will be taken of the donor area by appropriate cameras located on the robotic stand to establish the starting point values for each of the following. The total donor area as well as each individual drawn area on the scalp will be measured for (1) the total number of follicular units in the total donor area, (2) the total number of follicular units in each subdivided area, (3) the respective hair mass in the total donor area, (4) the total hair mass in each subdivided area, (5), a unevenness factor for the initial follicular unit distribution prior to the onset of the surgery (this is important for people who had previous FUE surgeries), (6) Each follicular unit will be analyzed for the number of hairs it contains along with measurements of the average hair thickness of each hair in the follicular units, (7) on a display screen, these measurements will appear and fixed for the surgeons evaluation. (8) once the surgery commences, ongoing measurements will be made in real-time, adjusted as each graft excision progresses. In this way the surgeon will understand the impact of the FUE upon the residual donor density, the residual donor hair mass, the unevenness factor for follicular unit distribution on a real-time basis. These ongoing calculations will be for the total donor area as well as each subset divided area defined by the lines drawn on the patient's head prior to the commencement of the surgery.

Anesthesia administered locally. Anesthesia in the form of a ring block will be administered prior to placing the tensioning belt on the patient's head.

Patient will be placed in special chair with virtual reality viewing in front of eyes that optimize (1) patient comfort and (2) the use of the belt tensioning means, which may be a tensioning belt (which is discussed below in connection with FIG. 7A) and/or tensioning pads that move in coordination with movement of the harvesting instruments (as discussed below in connection with FIGS. 7B and 7C). The special chair may be equipped with a breast plate to allow the patient to lean into the breast plate. As an extension of the breast plate of the chair (somewhat like a massage table, see FIG. 7D), are extension arms that extend upward to the level of the patient's forehead. These arms are bowed in such a manner as to not interfere with access to the recipient area of the head. A tensioning belt is connected to these arms to stabilize the patient's head. The area in front of the face may have a viewing area where virtual reality viewing in front of eyes can be used to watch movies, etc. during the procedure.

A special tensioning belt (described below in FIG. 7A) may be wrapped around the head to stabilize the head of the patient against a head rest and for patient comfort. The tensioning belt may further be constructed to facilitate mapping of the donor region and to facilitate graft excision although these are optional. On the part of the belt above the donor area of the scalp, there are tines that superficially go into the scalp (depth about 0.7 mm to 1.2 mm) to prevent the belt from slipping up or down. As the patient is anesthetized at this point, the tensioning belt will cause no pain to the patient nor will it damage the scalp's vascular integrity. Hanging from this belt are "rubber band"-like elastic cords that each contain a hook. There are many such cords hanging off of the belt over the donor area. These hooks are pushed into the high scalp to produce traction on the scalp, reducing scalp laxity. This stabilizes the scalp for follicular unit extraction (FUE), and decreases scalp laxity.

Thumbtack fiducial tines (TTFT) may be placed throughout the peripheral donor area for fiducials that will allow the computer and optical equipment to map out the donor area. These TTFTs will remain in place until all of the graft extractions are complete. This will allow the computer to map the exact location of each and every follicular group (graft) within the donor area before and after they are excised. These fiducials will be placed by the surgeon once the patient is placed into the special chair and the headband has been connected to the special chair. At the end of the graft extraction process, these TTFTs may be removed by the surgeon.

An example embodiment of thumbtack fiducial tines is described below. These are designed to be minimally invasive yet also to allow reproducible mapping and repositionings of automated harvesting devices, using computer and optical equipment to map out the donor area. For a completely non-invasive embodiment that allows reproducible mapping and repositionings of automated harvesting devices, pattern recognition techniques may be employed, whereby the donor region is imaged and the pattern of candidate grafts is stored as a pattern. Thereafter, the harvesting device is roughly positioned over the desired donor region, and fine positioning is achieved through pattern matching of the stored pattern against an actual image of the current donor region. After harvesting, the stored pattern is updated to reflect excision of the graft, thereby to enable future repositionings to the vicinity of the same donor region.

The surgeon views a large computer monitor that displays video information needed to assess and reassess the donor area as the FUE progresses. A baseline measurement is fixed and displayed in one area of the monitor. The surgeon will divide the donor area into zones, so that the video display is mapping the donor supply, both globally or by regional/zonal measurement. This is a dynamic process. There are algorithms that suggest various FUE densities and hair mass measurements for removing grafts, but the surgeon can change the algorithm upward or downward to create greater or lesser residual densities or hair mass measurements in the donor area as the grafts are removed. In addition, although the computer system will suggest optimum spacing for the extracted follicles to minimize confluence of missing follicular units, the surgeon can override this feature. If the number of grafts used for the total surgery is known, recommendations on graft distribution can be projected on the computer screen, to give the surgeon an insight as to the consequences of the surgical excision plan.

Once the anesthesia is complete, the headgear is positioned and the computer assessment of the donor area is complete, the surgeon brings his attention to implanting the grafts in the recipient area. He can request single, two hair, three hair or even larger numbers of hairs per graft, one graft at a time. Assuming that he wants to start by creating the leading edge of the hairline, he may request only single hair grafts.

One at a time, one or more robots at the back of the head will identify the area which the surgeon prioritized, and start removing, with a special punch, the requested grafts. With each graft excision, the graft will be transported by tubing from the donor area directly to the hand-held duplex implanter. Along the path of transport an optical detector inspects the graft for graft integrity. This process will take less than one second. The graft will then be implanted, by the surgeon or robotically. This is an iterative process and the surgeon will identify the number of hairs/grafts for each step of the FUE and the implantation process one at a time.

The surgeon may allow the computer to select the area for excision based upon calculations of residual donor densities and residual hair mass measurements in the areas chosen by the surgeon.

The surgeon may want to control how the robot(s) moves about the donor area; this is an option available to the surgeon to take more control of the decision process of the FUE component of the surgery.

At all times, the surgeon will be able to visualize, in digital graphic format, the residual donor density and the residual donor hair mass. The surgeon further can visualize, via data that records the area of abnormal spacing created by the extraction process, the degree of 'patchiness' created by the FUE process. Visualization is selectable by local area or globally.

Implantation can be performed with a hand-held implanter (see FIG. 1A) or remotely using a second set of robotic arms (see FIG. 1B). As the recipient area fills in, donor depletion of the donor area will be shown to the surgeon.

Implantation can be performed by a robot, using a plan created prior to the surgery. This plan will define, in advance graphically, the location where grafts of various sizes can be implanted.

Implantation Handpiece

Representative embodiments of implantation handpieces are discussed below. In general, these implantation handpieces include a generally cylindrical body for gripping by the surgeon, and first and second channels positioned on the cylindrical body. The first channel is connectable to a source of vacuum and the second channel is connectable to a source of harvested follicular units. A central rod and a hollow needle are provided, wherein the central rod and the hollow needle are positioned for slidable and relative movement of the rod inside the needle. In a retracted position of the rod relative to the needle, a harvested follicular unit is delivered from the second channel to an interior of the hollow needle under force of vacuum applied to the first channel at a position forward of the central rod. In an implantation position, slidable movement of the central rod relative to the hollow needle drives the follicular unit from the hollow needle into an implantation site.

In the context of control over graft on demand excision from the donor region, the implantation handpiece often plays a central role. When the surgeon holds it in his hand, for example, he actually controls everything. For example, the surgeon requests a 3-hair graft, the controller moves the robotic arm which holds an extraction tool to a selected zone of the donor region and to a site within the zone appropriate for excision of the requested graft in response to the command of the surgeon.

Figure 3:
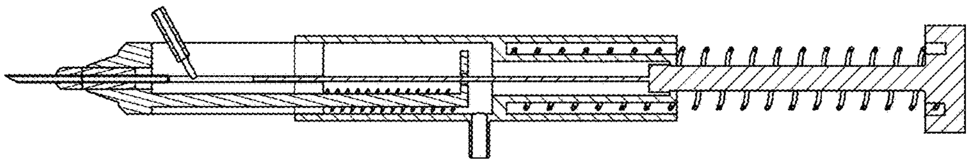
FIG. 3 depicts a first embodiment of an implantation handpiece.
Figure 3:
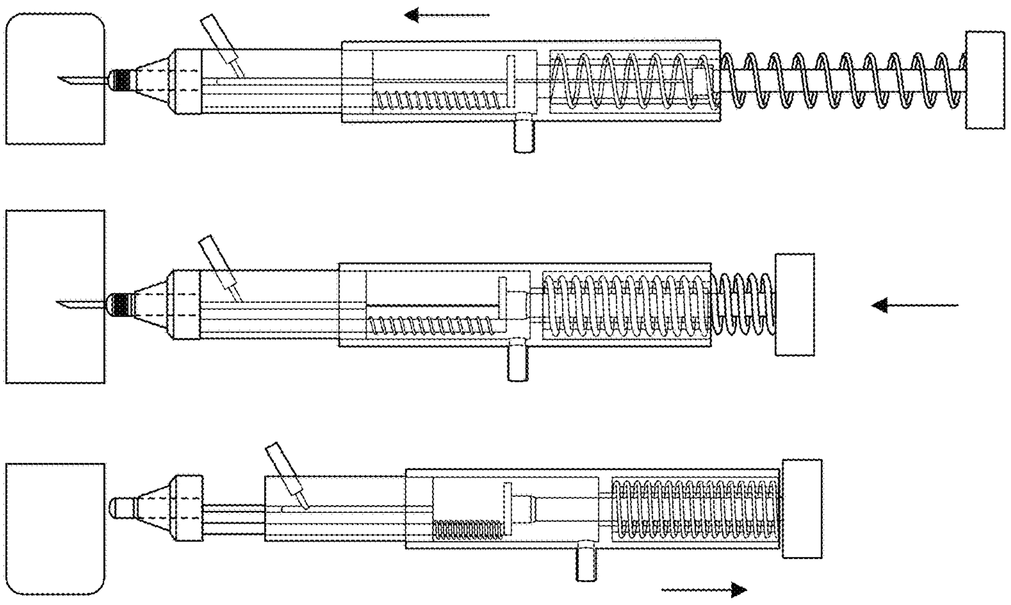

FIG. 3 depicts a first embodiment of an implantation handpiece. Herein, this embodiment is referred to as a “manual duplex”, the word “manual” signifying that the handpiece is operated by the surgeon manually using a plunger, and the word “duplex” signifying that two channels are provided to the handpiece, a first (rearward) channel connectable to a source of vacuum and a second (forward) channel connectable to a source of harvested follicular units.

Parts A, B and C of FIG. 3 depict the configuration of the manual duplex during an implantation cycle.

Figure 4A:
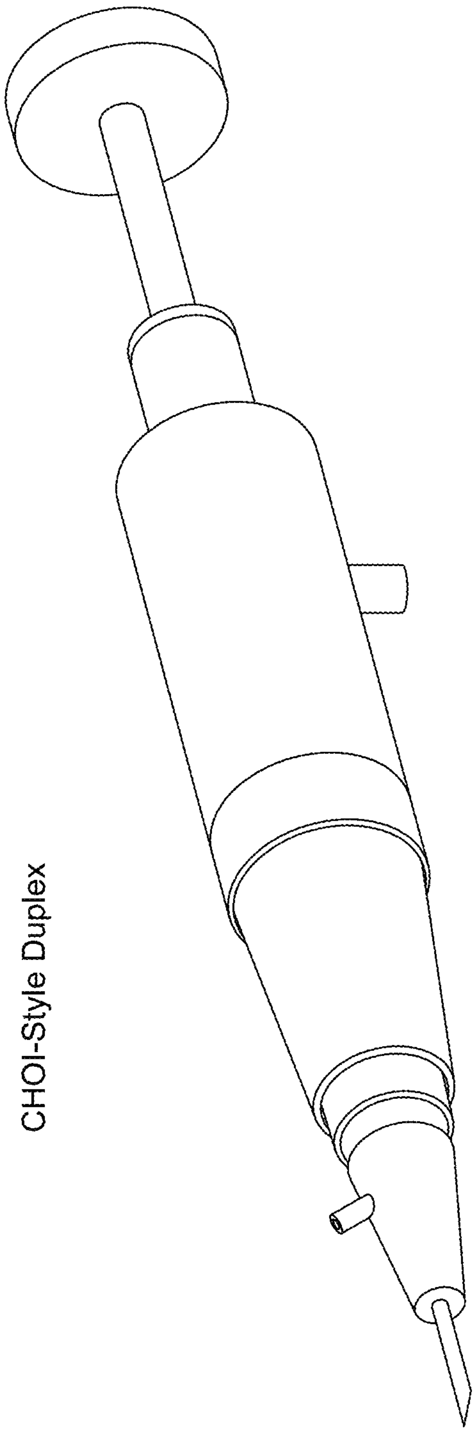
FIG. 4A depicts the outward appearance of a second embodiment of an implantation handpiece and FIG. 4B depicts a cross-sectional view thereof.
Figure 4B:
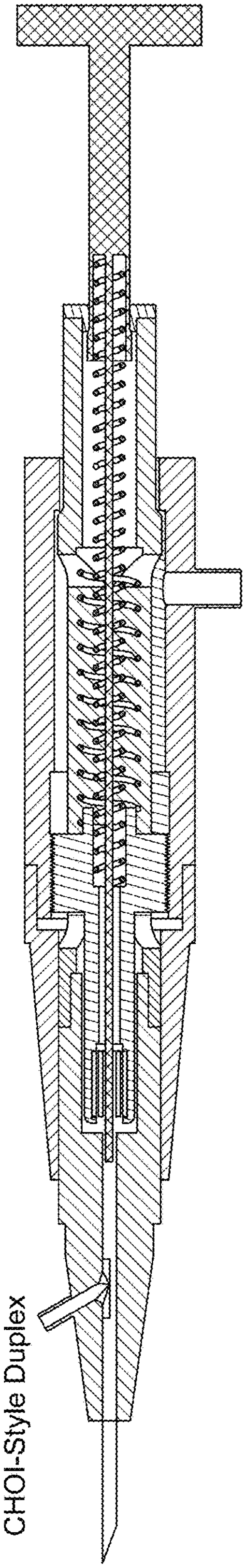

FIG. 4A depicts the outward appearance of a second embodiment of an implantation handpiece and FIG. 4B depicts a cross-sectional view thereof. The embodiment depicted in FIGS. 4A and 4B is herein referred to as a “modified Choi-style” handpiece. The word “modified” signifies that significant modifications have been made to a Choi-style manual implantation handpiece.

In particular, modifications shown in FIG. 4A to a Choi-style manual implantation handpiece include the addition of two channels to the handpiece, a first (rearward) channel connectable to a source of vacuum and a second (forward) channel connectable to a source of harvested follicular units. In addition, the central rod is modified so that in the retracted position the central rod is fit loosely inside the hollow needle. The first channel is positioned at a rearward side of a forward end of the central rod and the second channel is positioned at forward side of the forward end of the central rod. The fit of the central rod inside the hollow needle is sufficiently loose as to allow vacuum applied from the first channel to reach alongside the central rod and to suction a harvested follicular unit from the second channel.

Figure 4C:
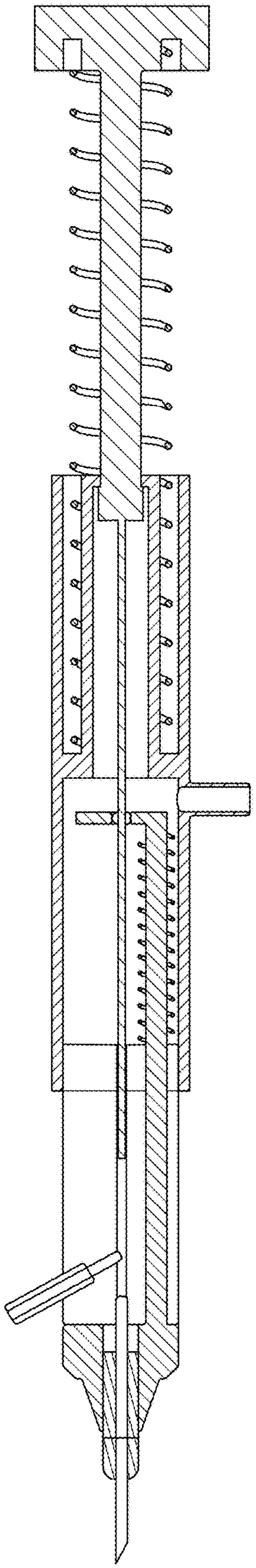
FIG. 4C depicts a manual duplex handpiece for comparison with the modified Choi-style handpiece of FIGS. 4A and 4B.

FIG. 4C depicts a manual duplex handpiece for comparison with the modified Choi-style handpiece of FIGS. 4A and 4B.

Figure 5:
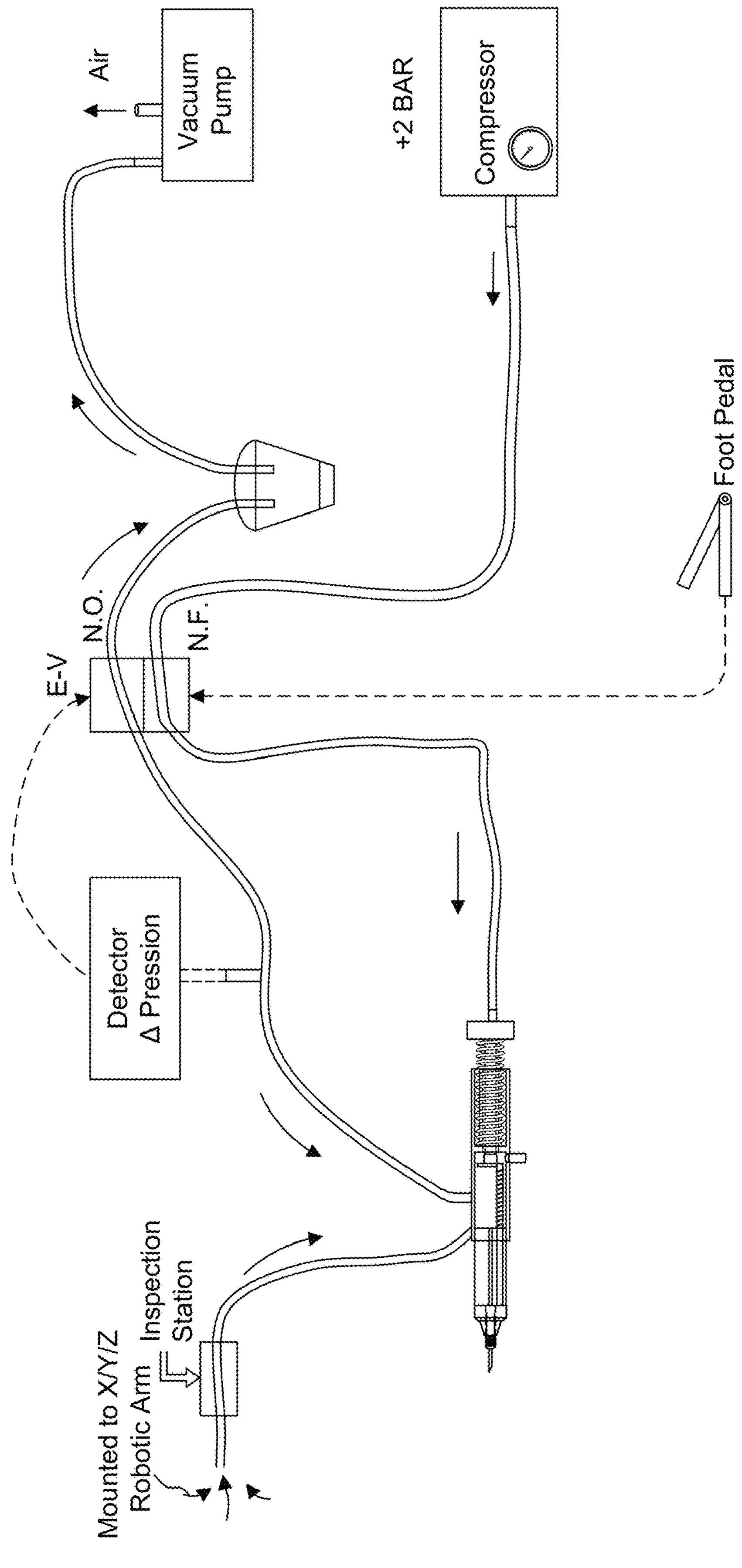
FIG. 5 depicts a third embodiment of an implantation handpiece.

FIG. 5 depicts a third embodiment of an implantation handpiece. The embodiment depicted in FIG. 5 is herein referred to as a “pressure-actuated duplex,” wherein the words “pressure-actuated” signify that relative to the manual duplex of FIG. 3, there is a third channel for controllable introduction of pressure under control of the surgeon, wherein introduction of pressure from the third channel drives the central rod from the retracted position to the implantation position, resulting in implantation of the follicular unit.

Saline Infusion

Figure 6:
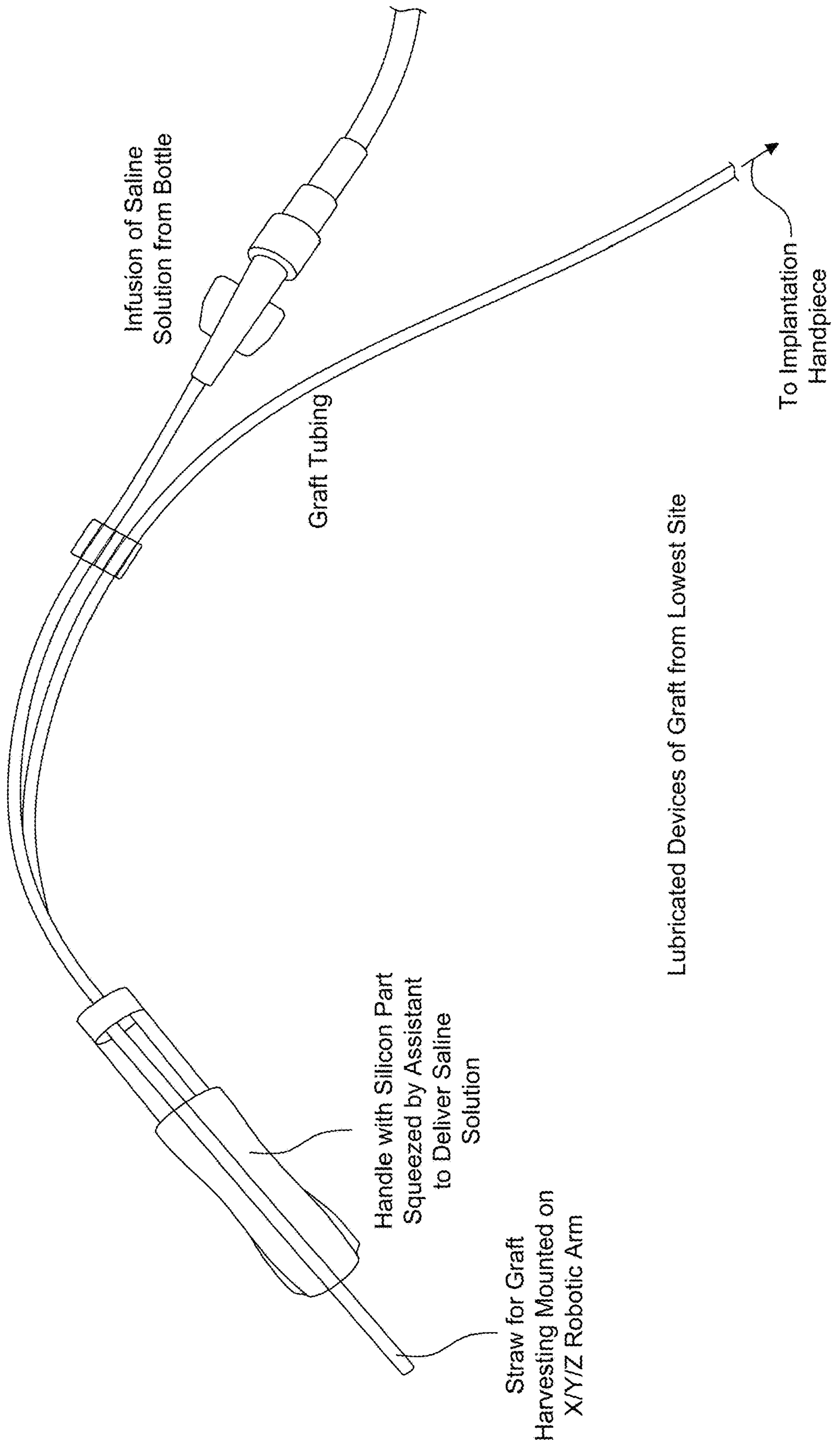
FIG. 6 illustrates infusion of saline to facilitate delivery of harvested follicular units to the implantation handpiece.

FIG. 6 illustrates infusion of saline (or another appropriate solution) to facilitate delivery of harvested follicular units to the implantation handpiece.

As illustrated in FIG. 6, a source of saline is introduced to the tubing of FIG. 1, in the vicinity of the punch harvesting instrument, so to enhance the effectiveness of suction in the aspiration of harvested grafts to the implantation handpiece, to ensure that grafts are fully excised from the donor region, and to lubricate the interior of the delivery tubing thereby lessening the possibility of damage to the graft during delivery of the harvested follicular unit to the implantation handpiece and reducing the possibility of clogging of the tubing by the graft.

Saline may also be used in a number of other ways to facilitate excision and delivery of excised grafts to the implantation handpiece. For example, saline may be injected around the donor graft as the harvesting punch is making its incision. The injection of saline around the donor grafts helps to facilitate deep detachment from the skin when the graft is harvested by suction. As another example, a small amount of saline may be injected into the donor region of the scalp immediately adjacent to the targeted graft just before the punch actually pierces the skin at the donor site. The saline can be injected in the general area where the work is being performed by the punch, or is injected specific to the follicular unit targeted for harvesting and excision, such as within 1.0 mm or less of the punch excision site. The injection of saline into the scalp increases tumescence/hardness of the donor region, often resulting in a punch that can perform better.

The straw illustrated in FIG. 6, will only be used if the implanter is used independently, without the Graft on Demand Robotic System (GODR) described herein. In normal operation for the full GODR, the tube that is discussed in FIG. 6, will be connected directly to the implanter by appropriate tubing as illustrated in FIG. 5.

Tensioning Belt

FIG. 7A illustrates a tensioning belt for application to a donor region of the scalp, for stabilizing the head of the patient against a head rest and for patient comfort. The tensioning belt includes means for fixing the band to the headrest that supports the head of the patient during harvesting of grafts from the donor region. Such means for fixing the belt to the headrest include an easy release of this mechanism (a) to prevent injury to the patient, (b) to allow the patient to take a restroom break, (c) to attend to other medical issues.

As illustrated in FIG. 7A, the tensioning belt is further constructed with hooks to produce traction on the donor region of the scalp and to reduce scalp laxity, thereby to facilitate graft excision, and is further constructed with fiducial marks to facilitate mapping of the donor region. It should be understood that use of hooks and fiducial marks is optional, particularly in cases where a primary use of the tensioning belt is to stabilize the head of the patient and/or for patient comfort.

Briefly, as depicted in FIG. 7A, a tensioning belt includes a flexible band of suitable length to wrap around the head of the patient at frontwise position slightly above the patient's eyebrows to a rearwise position at the crown of the patient's scalp. This same belt can be connected to a headrest that the patient uses to lean into. In combination, the belt and the headrest, will minimize head movement during the extraction of the grafts. Plural fiducial marks may be fixed to the band by which specific follicular units in the donor region are reproducibly locatable, and plural tines extend from the band for anchoring into an upper region of the scalp, above the crown. Plural elastic cords extend from the band, each such elastic cord terminating in a hook, wherein the hooks are constructed to punch into the high scalp below the band and above the donor region to produce traction on the donor region of the scalp and to reduce scalp laxity. The hooks can be connected to each other by a bar, making their use easier than one by one use individually.

In a priority document for this case, the width of the belt in FIG. 7A was exaggerated. In this document, the width of the belt is shown correctly narrowed.

Tensioning Pad

In a manual harvesting session according to conventional technique, the surgeon often places the thumb of the non-dominant hand against the scalp and moves the thumb away from the donor site selected for extraction, to create and to produce tension on the scalp in the vicinity of the donor region. This creates local traction in the scalp in the vicinity of the donor follicular unit, and aids the surgeon while making the initial incision into the scalp around the follicular unit, resulting in more successful excisions.

According to embodiments herein, a tensioning pad may be provided to tension the scalp in the vicinity of the donor region. The pad has a small footprint, approximately 1.0 to 2.0 sq. cm, with a contact side thereof constructed for engagement with and tensioning of the scalp. To ensure that the tensioning pad engages sufficiently with the scalp so as to be capable of lateral stretching scalp during harvesting, the surface of the contact side of the pad may be roughened or may be fitted with small penetrating or non-penetrating tines.

FIGS. 7B-1 through 7B-5 illustrate one example embodiment of a scalp tensioning pad. In this embodiment, the scalp tensioning pad 75 is fitted with small and non-penetrating tines 76 for engagement with scalp 77 in the vicinity of the donor region. The tensioning pad 75 is mounted via rod 74 to an auxiliary robotic arm (a tensioning robotic arm) for independent and coordinated movement of the scalp tensioning pad in coordination with movement of the robotic arm for the harvesting instrument. Pad 75 may be mounted to rod 74 via an articulated mounting, so as to allow for slight angular movement of pad 75 relative to rod 74, to accommodate curvature of the scalp.

In these diagrams, only the punch 71 of the harvesting instrument is depicted, the punch 71 terminating in a flared trumpet tip 72. The punch 71 is mounted to the chuck of a rotational harvesting instrument (unshown) which in turn is mounted to its own separate robotic arm as depicted in FIGS. 1A and 1B.

These figures show a sequence of operations for extraction of a follicular unit 78 from scalp 77 of a patient. The figures are highly magnified.

In these figures, a hollow extraction punch 71 has a flared tip 72 and is controlled by an unseen robot arm. Rod 74 supports a pad 75 (which may be on an articulated mounting) and small tines (or pins) 76 project from the pad. The rod/pad assembly is also controlled by an unseen robot arm.

Scalp 77 of a patient has multiple follicular units 78 of which some are harvested using the punch.

In FIG. 7B-2, the rod 74 is extended by the tensioning robotic arm, independently of movement of the harvesting instrument and its punch 71, until pad 75 and tines 76 contact with the scalp. In FIG. 7B-3 the rod is moved by the tensioning robotic arm laterally away from the follicular unit that has been targeted for harvesting (in this diagram, movement is upwardly away from the follicular unit). Because of the tines 76 the scalp under pad 75 moves upwardly with it, causing tension in the stretched scalp. In FIG. 7B-4, the punch 71, which is rotating and/or vibrating due to being fixed in the chuck of the harvesting device, is repositioned and cuts into the scalp, surrounding follicular unit 78. In FIG. 7B-5, punch 71 is retracted with the excised follicular unit inside it. The harvested follicular unit is then delivered via tubing to the implantation handpiece, as depicted in FIGS. 1A and 1B.

Figures 1, 2, 3, 4, 5, 7C:
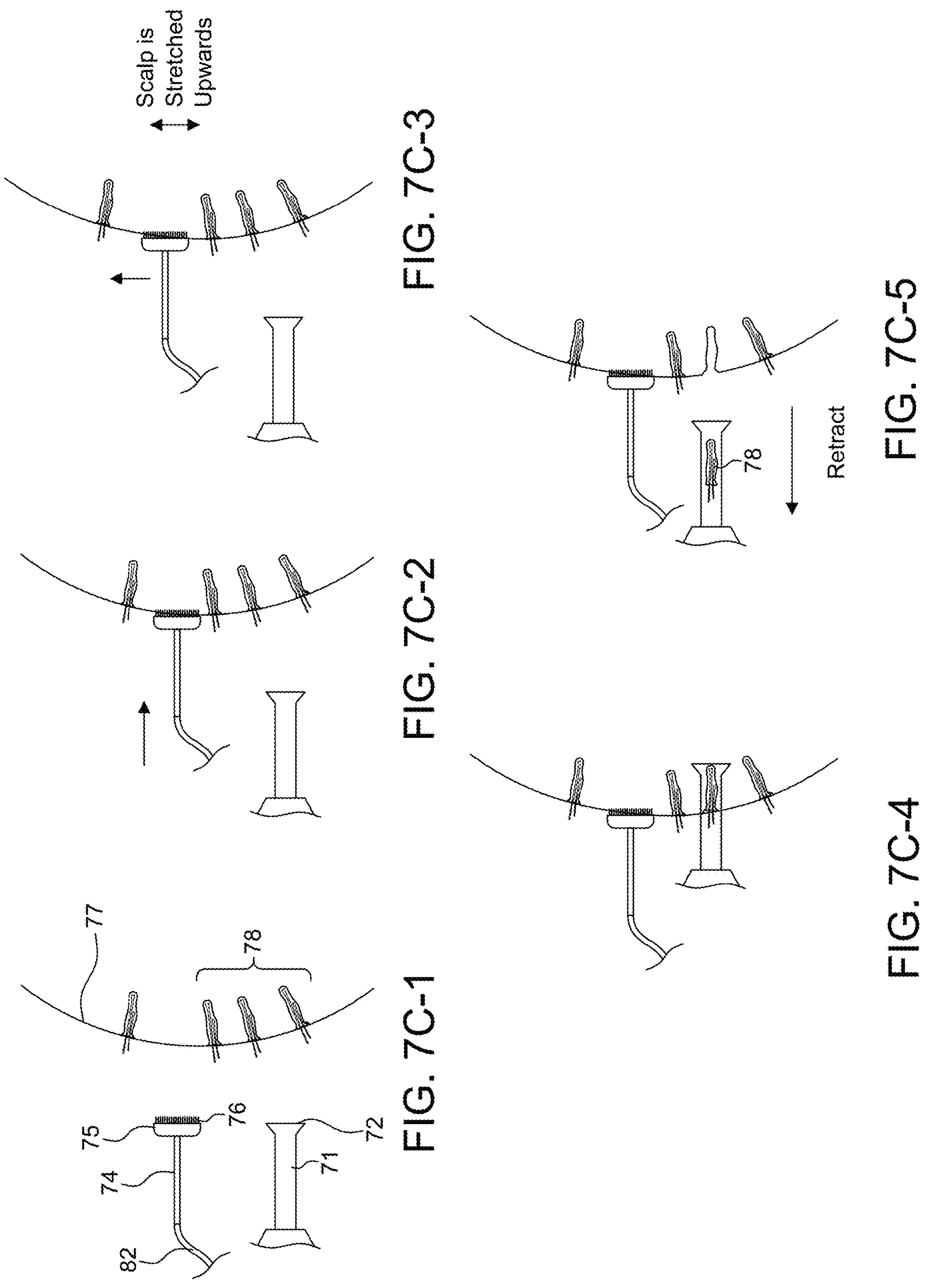
Figures 6, 7C:
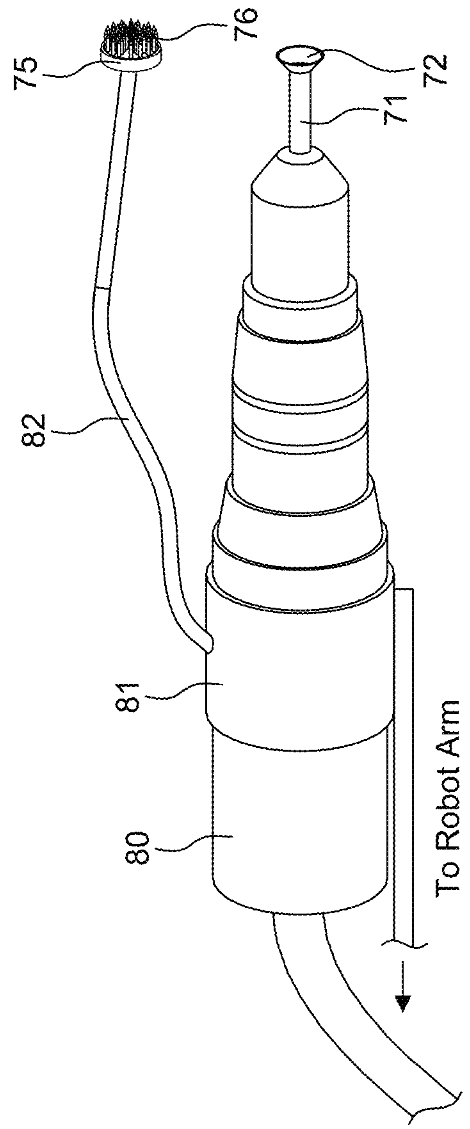

FIGS. 7C-1 through 7C-6 illustrate another example embodiment of a scalp tensioning pad. In this embodiment, a scalp tensioning pad 75 is mounted by a flexible or non-flexible arm 82 to the same robotic arm for the harvesting instrument for movement in coordination with movement of the robotic arm.

In these figures, like those in FIGS. 7B-1 through 7B-5, the surface of the contact side of tensioning pad 75 is constructed for engagement with and tensioning of the scalp, here with small non-penetrating tines 75. The tensioning pad 74 is attached to the extraction handpiece and both are moved together by the robot arm. The attachment is via a flexible arm 82 which is slightly curved and resiliently flexible.

FIG. 7C-6 shows the overall arrangement, and in particular depicts a handpiece 80 with a clamp 81 for attachment to the robot arm, and with a flexible rod 82 attached to the clamp and supporting the pad-pin assembly. As in FIGS. 7B-1 through 7B-5, the harvesting instrument is an extraction handpiece 80 having punch 71 terminating in a flared trumpet tip 72 mounted to a chuck of handpiece 80. The punch 71 is mounted to the chuck for rotational and/vibratory movement of punch 71 by the harvesting instrument which is mounted to a robotic arm as depicted in FIGS. 1A and 1B. Pad 75 may be mounted to rod 74 via an articulated mounting, so as to allow for slight angular movement of pad 75 relative to rod 74, to accommodate curvature of the scalp. With this configuration, the harvesting instrument and the tensioning pad move together as one unit, with bending of the flexible arm 82 providing for a tensioning effect on the scalp as described below.

More particularly, FIGS. 7C-1 through 7C-5 figures show a sequence of operations for extraction of a follicular unit 78 from scalp 77 of a patient. The figures are highly magnified. As shown in these figures, the pad 75 is initially positioned forwardly of tip 72 of the extraction punch 71.

In operation, as the robot arm advances toward the scalp, the pad 75 contacts the scalp first, due to the forward positioning of pad 75 relative to tip 72 of the punch. This initial contact is depicted in FIG. 7C-2. As the robot arm continues to advance, the curve in the flexible rod bends further, as shown in FIG. 7C-3, causing pad 75 to move superiorly away from the follicular unit that has been targeted for harvesting (in this diagram, movement is upwardly away from the follicular unit, however, in other parts of the body, traction may be required in almost any direction). Because of the tines 76 the scalp under pad 75 moves upwardly with it, causing tension in the stretched scalp.

In FIG. 7C-4, the robot arm continues to advance at which point the extraction punch 71 contacts the scalp, and penetrates. The flexible rod may be maintained in this position for one or more extractions if adequate tension is sufficient for multiple graft extractions, of they both can be retracted, with the harvested graft 78 inside the punch. The harvested follicular unit is then delivered via tubing with suction to the implantation handpiece, as depicted in FIGS. 1A and 1B.

Head Stabilization

Figure 7D:
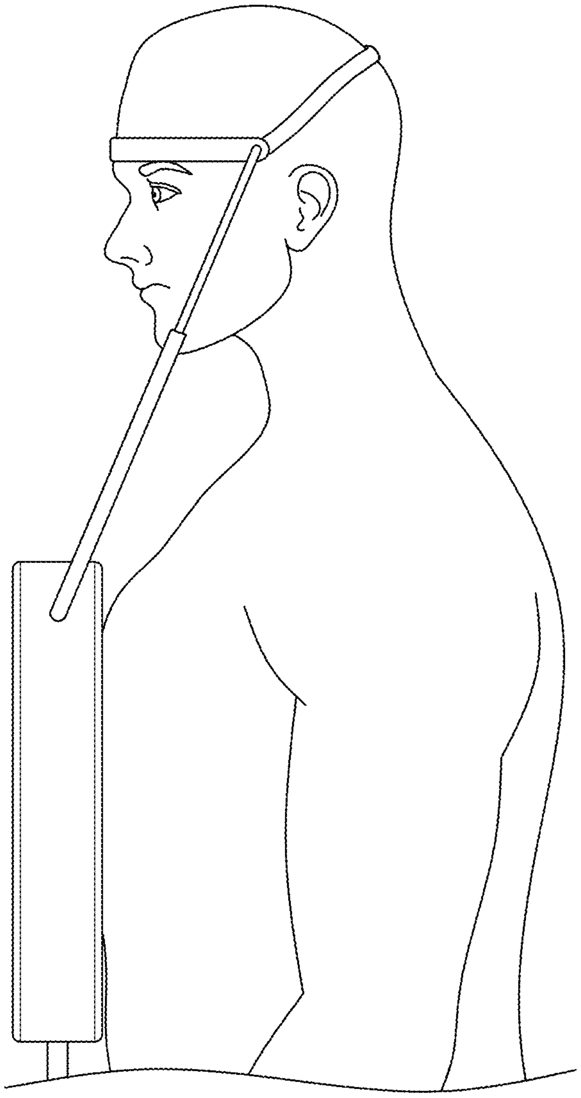
FIG. 7D is a view depicting a mechanism to stabilize the head of the patient during a transplant procedure.

FIG. 7D is a view depicting a mechanism to stabilize the head of the patient during a transplant procedure.

As shown in FIG. 7D, a patient seated in a slightly forward upright pose with chest against a chest rest and head supported by a rigid or semi-rigid semicircular headrest. The headrest may be padded for additional patient comfort.

Extending from the chest rest are two rigid arms that support the semicircular headrest. The lengths of the arms are adjustable to accommodate patients of different sizes. In this embodiment, there is a locking telescopic arrangement along the length of the arms to allow for adjustment.

The head rest is a half-circle against which the area just above eyebrows of the patient is supported, with the frontal forehead of the patient completely uncovered. A flexible fixation strap extends from one side to the headrest, around the patient's head, to the other side of the headrest. The fixation strap is adjustable to accommodate differences in head circumference, and is adjustably fixed to one or both sides of the headrest, with a quick-release capability for patient safety. In this embodiment, Velcro pads are used for quick release fixation. The fixation strap wraps around the back of the patient's head, to fix the head against the head rest. The fixation strap is positioned just below the crown of the head leaving the occipital region completely exposed.

Thumb Tack Fiducial

Figure 9:
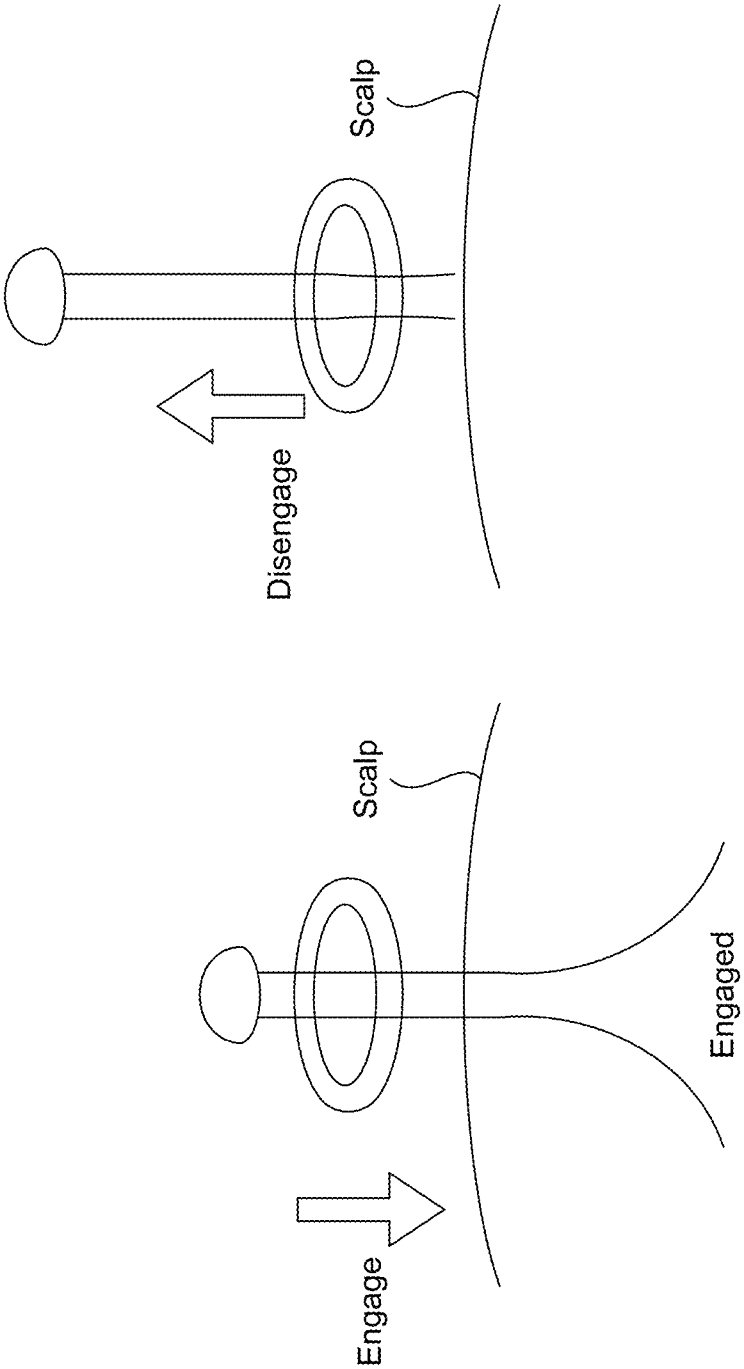
FIG. 9 depicts a thumb tack fiducial constructed for fixation to the donor region so as to facilitate accurate and reproducible repositioning of the harvesting instrument using machine vision.

FIG. 9 depicts a thumb tack fiducial constructed for fixation to the donor region so as to facilitate accurate and reproducible repositioning of the harvesting instrument using machine vision.

In FIG. 9, the left-hand view is a view showing the fiducial engaged with the epidermal skin of the donor region, and the right-hand view is a view showing disengagement.

More particularly, as depicted in FIG. 9, the fiducial includes a small diameter (approximately 5 mm) tack-like structure from which two needle-like legs extend downwardly. The tack is constructed for insertion into the donor region of the patient. The needle-like legs are biased outwardly so that they spread outwardly as the tack is inserted below the skin into the donor region. A slidable retainer ring encircles the legs and is positioned so that before insertion of the tack into the donor region the legs are retained in a vertical orientation, against the outward bias of the legs.

As the tack is inserted into the donor region the retainer ring slides upwardly allowing the legs to extend outwardly underneath the surface of the donor region which in this embodiment is the scalp. The legs extend into the scalp superficially to a depth of approximately 1.0 to 1.5 mm, penetrating through the epidermis but so not deeply into the dermis as to reach down to sebaceous glands or to draw significant amounts of blood. This depth is enough to ensure that the tack remains fixed to the scalp despite movement of the head (the donor region) but not enough to cause post-surgery injury or wounds.

Figure 10:
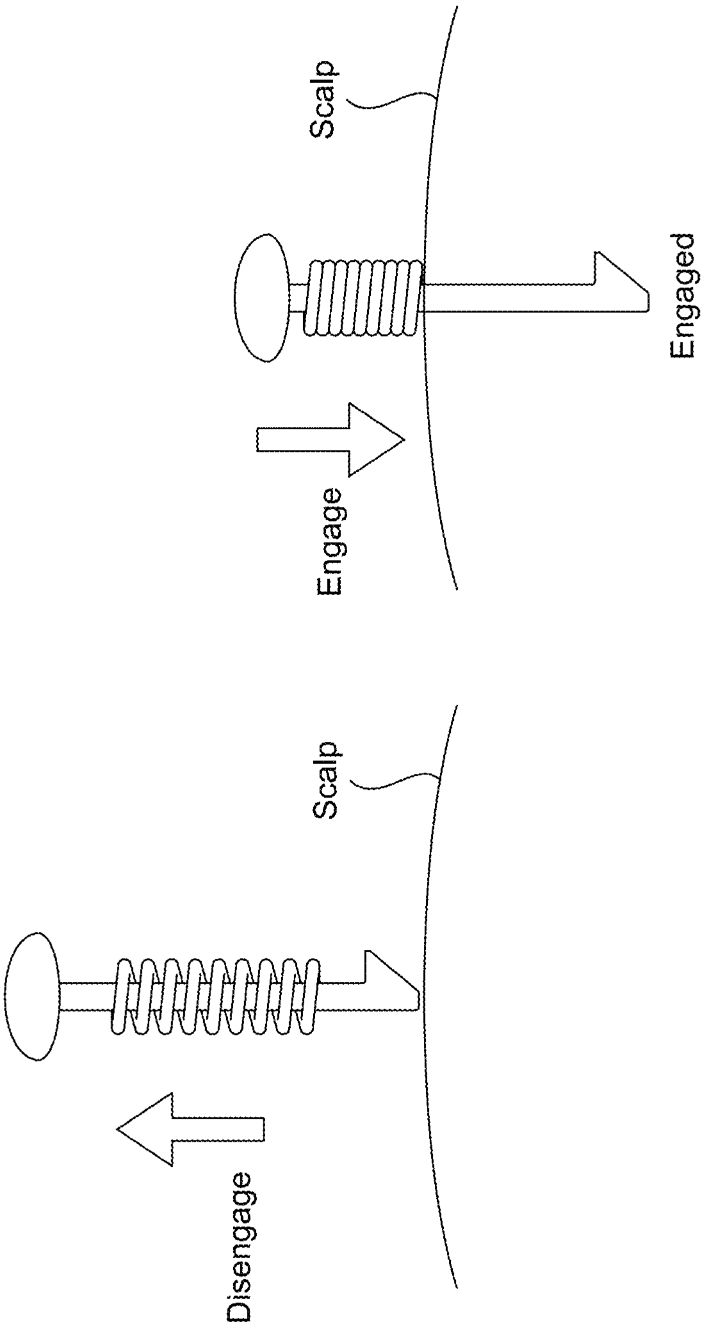
FIG. 10 depicts another embodiment of a thumb tack fiducial using a spring-loaded fishhook construction.

Other iterations of the thumbtack can use a spring-loaded fish-hook device or a screw type device to insert into the scalp, as illustrated in FIG. 10.

On the diameter surface of the tack a fiducial mark is formed, such as a one-dimensional bar code or a two-dimensional QR code.

During harvesting, several thumb tack fiducials, each with a different code, are applied across the donor region. For example, the fiducials may be applied to define the boundaries of each of multiple zones of the donor region. Since the fiducials are applied directly to the skin of the donor region, the fiducials facilitate accurate and reproducible repositioning of the harvesting instrument using machine vision, even if the donor region has been moved. For example, during a transplant procedure, the patient may need a short break, necessitating a release from the headrest support. After the patient's return, the head will naturally be positioned slightly away from the pre-break position. However, the fiducials themselves are still in the same position, thus allowing machine vision to accurately resume harvesting positions.

It is also possible to use the fiducials in the implantation region, for the same purpose of accurate and reproducible positionings of the implantation handpiece, particularly in embodiments such as those depicted in FIG. 1B where the implantation handpiece is manipulated remotely.

The fiducials may be provided in a sterilizable kit together with other pieces used during a procedure, such as the fixation strap used for head stabilization.

Depletion Monitoring

Figure 8A:
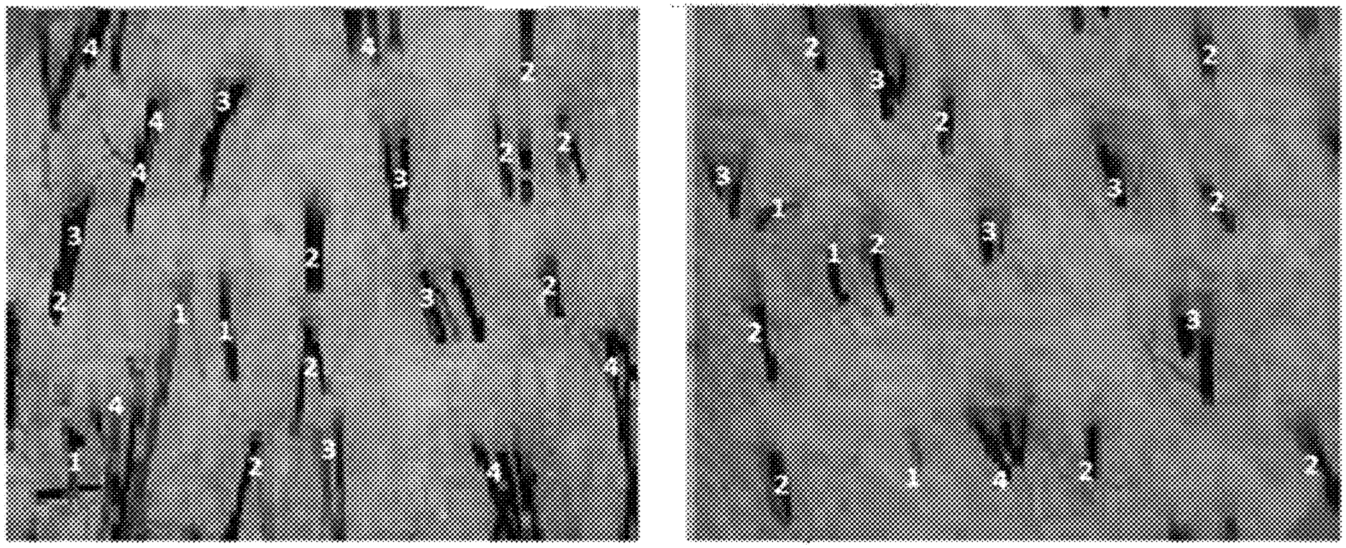
FIGS. 8A and 8B illustrate a representative displays of depletion monitoring of the donor region.

FIG. 8A illustrates a representative display of depletion monitoring of the donor region. Multiple fiducials may be placed in or on the donor area (scalp) along the margins of the donor area.

More particularly, the donor region of the scalp, as designated by the surgeon, is typically divided into zones, given that each different zone in the donor region has differing statistical content of candidate grafts and candidate density and candidate color. In one example, the donor region is divided into sixteen (16) zones, such as shown in FIG. 8C, which shows a donor region of the scalp sized 6 cm by 28 cm, divided into 16 numbered sections During surgery, the zones of the donor region are depleted as grafts are harvested. In this embodiment, the selection of which grafts to harvest is made by computerized algorithms and formulae, designed to ensure that graft removal is evenly distributed across the donor region in proportion to the distribution of candidate grafts in each zone of the donor region. The surgeon may input the number of 1,2 and 3 (or more) hairs grafts he/she wishes to extract. Calculations are therefore easily made across all areas for distributing the extractions in the least harmful manner. Nevertheless, for safety and patient-protection purposes, as well as for purposes such as ensuring good appearance of the donor region post-surgery, the surgeon may decide to override automatic selection. Depletion monitoring as described herein provides the surgeon with a tool to decide if an override is advisable.

While depletion monitoring as described herein pairs well with automated harvesting of grafts, it is to be understood that depletion monitoring may be used in circumstances other than automated harvesting, such as in transplant procedures where grafts are harvested manually or even independently as a diagnostic or planning tool to help the surgeon in decision making.

When harvesting beard hair below the chin or in the pubic area, the goal may be to remove all of the grafts present in these areas. In this case, the depletion goal might be 100%, something that would never be the situation with scalp harvesting where depletion limits impact the donor areas appearance, leaving enough donor hair to prevent a see-through or balding appearance of the donor area.

Briefly, according to embodiments described herein, depletion of hair grafts from a donor region of a patient's scalp during transplant surgery is monitored by imaging the donor region of the scalp, such as with a vision system, wherein the donor region being divided into a plurality of zones, and by storing initial statistical content of candidate grafts in each of the plural zones, wherein the initial statistical content is collected automatically at a time prior to commencement of transplant surgery. Candidate density will also be measured in each such zone. Ongoing statistical content of candidate grafts in each of the plural zones is gathered, wherein the ongoing statistical content is collected automatically at a time during harvesting of grafts from the donor region during transplant surgery and includes real-time candidate density in each such zone. A visual depiction is displayed to the surgeon for comparing the initial statistical content and the ongoing statistical content for one of more zones of the donor region in real time during transplant surgery. The illustrated display is but one embodiment of graft depletion monitoring.

A computer screen may further include the display of current images of zones of the donor region in comparison with initial images of zones of the donor region. In addition, on images of zones of the donor region, the display may further superimpose information designating characteristics of each candidate, the characteristic information including at least the number of hairs in each candidate.

Thus, as shown in FIG. 8A, the display includes an upper portion showing statistical information and a lower portion showing images of the donor region. In this example, the upper portion is displaying a subset of the statistical information for each of two different ones of the sixteen zones of the donor region. Here, zone 12 appears on the left and zone 9 appears on the right. The statistical information includes candidate density in the zone, average hair thickness and donor hair mass in the zone shown. The statistical information is given in the subset at both of two areas of the 16 divided areas prior to the onset of the surgery. A subset of the zones is displayed to reduce the complexity of illustration in this patent.

The statistical information may include one or more than one of the following statistical metrics.

Figure 8B:
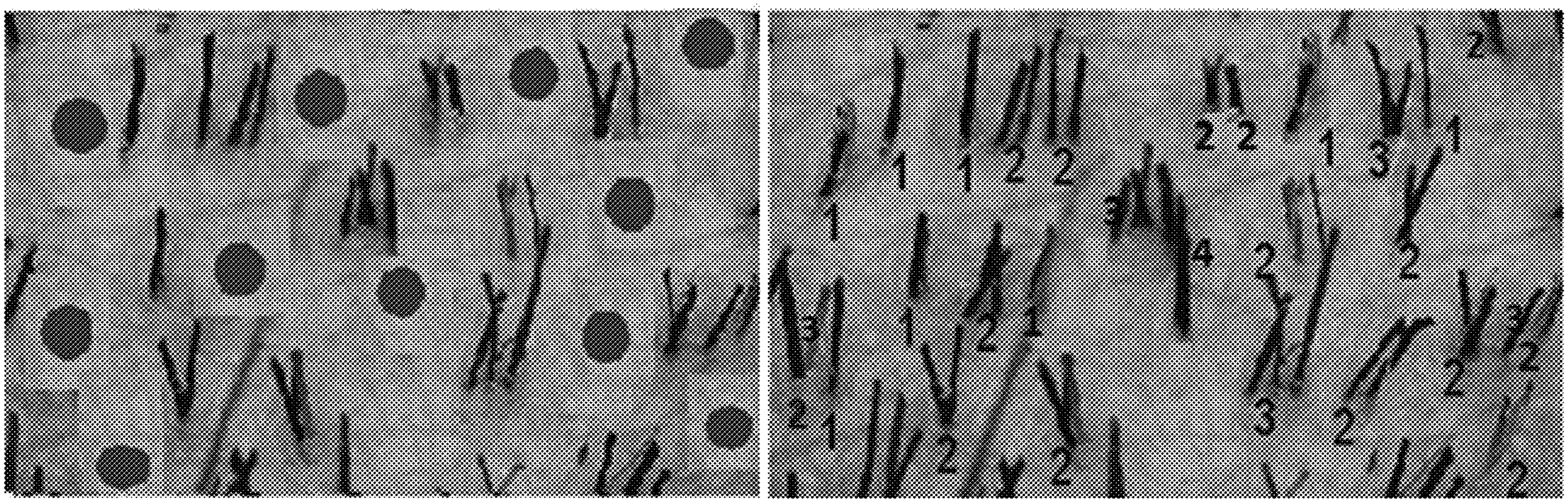
Figure 8C:
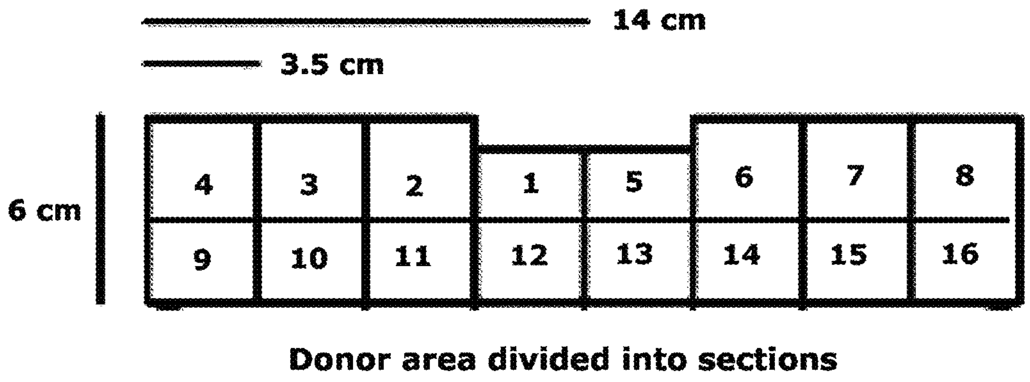
FIG. 8C depicts the division of the donor region of the scalp divided into sections.

- Hair Mass: a single hair based upon the thickness in microns multiplied by $A=\pi r^2$ multiplied by the number of hairs measured in the field calculated (e.g., a subset of one of 16 areas or the entire head shown in FIG. 8A and FIG. 8B).
- Regional Hair Mass: the sum of all of the hairs in one of the active 16 areas where the active FUE area=the thickness in microns multiplied by $A=\pi r^2\times$number of hairs/divided by 1000 to convert to mm
- Donor Hair Mass: The sum of all of the hairs on the donor area of the head as outlined by the surgeon, multiplied by the thickness in microns of all of the hairs multiplied by $A=\pi r^2\times$number of hairs/divided by 1000 to convert to mm
- Regional Donor Density: The density in one area that is worked on (an actual subset active area and calculated by #hairs/#follicular units in the field of view.
- The Entire Donor Density: Calculated by #hairs on the entire donor area of the scalp/#follicular units in the donor area if measured, or it is extrapolated from the donor area to the entire head, calculated by #hairs/#follicular units in the field of view. A typical Caucasian has 110,000 hair on the scalp and 50,000 follicular units. The Donor density for an average Caucasian is 110,000/50.000=2.2 hairs per follicular unit. The typical donor area has 12,500 follicular units or 27,500 hairs. When calculated, this translates to 2.2 hairs per follicular unit. The numbers used here are known average number for a typical Caucasian male.

In the preparation of FIGS. 8A and 8B the following assumptions were made.

The average Caucasian has 50,000 follicular units on his head, which is the calculation used in FIGS. 8A and 8B.

Hair Mass has no unit of measure (such as length or area); it is just a way to compare the value of individual hair thickness as one hair is added to the rest of the hairs in the active field of view, or on the entire head if shaved. If it did have a unit of measure, the length of individual hairs would be found in the calculations of Hair Mass being more realistic (not practical), but not from a hair transplant surgeon's point of view. There is an assumption in these examples, that the entire head was shaved so that measurements could be taken for the reference number on the top of FIGS. 8A and 8B. The donor area, therefore, must be closely shaved on these patients to obtain the reference numbers in the examples. If the entire head is not shaved, then the calculations can be made from the Donor area alone. Moreover, the hairs within the Follicular Units in the donor area are generally uniform in thickness; however, that may not always be the case. Clearly, if some of the hairs are thinner within the Follicular Unit, then the Hair Mass of that Follicular Unit will be decreased. Many small cameras may be used to view the donor area from different directions, and there will be enough of them to image each hair in the Follicular Unit and be able to calculate Hair Mass along with other calculations. As for head size, knowing the size of the Donor area, head size can be reasonably estimated.

Global Hair density was assumed to be calculated (in the Figures) before the onset of the surgery on a completely shaved patient's head, as discussed above.

In the lower portion of the example of FIG. 8A, there are images of two of the zones as selected by the surgeon (both are subsets of the zones for illustrative purposes). The images show two different zones selected by the surgeon. These reflect the initial state of the zone prior to the beginning of the FUE surgery. For illustrative purposes, the numbers per graft were written over each follicular unit (graft); however, this may not be the way the display will be programmed. Even though the number of follicular units (graft) are different between the two areas, the donor density shows a difference in the density between the two areas. Having a lower density above the ears, when compared to the back of the head, is not uncommon. The surgeon can move the field of view from one area to another. In this example, a baseline irregularity index for both areas may be provided (not shown).

Superimposed on the images are indicators designating characteristics of each follicular unit candidate. In this embodiment, the indicator signifies the number of hairs and grafts in each candidate globally for the entire head if it is shaved, restricted to the donor area as a whole (not shown) or for each one of 16 areas marketed by the surgeon. The marking of the donor area. In other embodiments, characteristics of the candidate can include color of the candidate's hair and skin, width of the candidate hair shafts, angle of the candidate's hair as it exits in the scalp, the thickness of individual hairs within a graft at any individual measurement, or across one of the 16 zones of the donor area or across the entire donor area, and even to the entire head based upon overall dimensions of the head and surgical excision field, and so forth.

FIG. 8B illustrates another representative display of depletion monitoring of the donor region. Multiple fiducials may be placed in or on the donor area (scalp) along the margins of the donor area or pattern recognition can be used to orient the robotic arms appropriately.

As shown in FIG. 8B, the display includes an upper portion showing statistical information and a lower portion showing images of the donor region. In this example, the upper portion is displaying statistical information for a designated one of the sixteen zones of the donor region, as selected by the surgeon as the current donor region. The statistical information includes candidate density in the zone, average hair thickness and donor hair mass. The statistical information is given at both of two times: the current state of the zone (figure left) and the pre-operative (baseline) state of the zone (figure right), so as to permit the surgeon to compare the initial statistical content and the ongoing statistical content. In this example, the systems computer calculates the percentage of depletion recorded in real-time for the surgeon to view. Also note the data reported in the computer image records the depletion amount of hair in hair mass in real-time. The computer estimated that 32% of the hair mass has been removed in this Figure on the left. With good computer suggestions, high hair mass depletions, such as depletions in patients with preoperatively very low hair mass, would be damaged if more than 20% of the hair mass should be removed. This would produce the appearance of balding in the donor area. This gives the surgeon a tool to optimize the extractions according to the plan the surgeon put together with the patient.

In the lower portion of the example of FIG. 8B, there are images of the designated one of the zones as selected by the surgeon (here, "zone 1"). On the right, there is a historical initial image of the zone and on the left there is a current image of the zone, i.e., an image which depicts harvesting already performed. Illustrated in real-time on the left-hand image is the current state of the zone which show the sites of previous excisions of grafts. Superimposed on the right-hand image of the initial (baseline) state of the zone are indicators designating the number of hairs in each of follicular units. This illustration was made to demonstrate the counting of the individual hairs in each follicular unit. In this embodiment, the indicator signifies the number of hairs and grafts in each candidate. In other embodiments, characteristics of the candidate can include color of the candidate's hair and skin, width of the candidate hair shafts (which vary within a single follicular unit), angle of the candidate's hair as it exits in the scalp, the average thickness of individual hairs within a graft, overall dimensions of the head and surgical excision field, and so forth.

The embodiments illustrated and discussed in this specification are intended only to teach those skilled in the art how to make and use the disclosure herein. The size of the areas shown in FIGS. 8A and 8B were intentionally reduced in size for illustrative purposes. It will be understood that the features of the various embodiments may be combined, for example, combined manual and the use of robot-assisted implantation.

Automated Selection of Grafts for Harvesting

As indicated above, selection of which grafts to harvest is made by computerized algorithms and formulae, designed to ensure that graft removal is generally distributed evenly across the donor region in proportion to the distribution of candidate grafts in each zone of the donor region.

One objective for selection of grafts for harvesting is to preserve the appearance of the donor region after harvesting of grafts is completed. Some research has indicated that for a donor region in the occipital area of the scalp, at least a density of 100 hairs per cm^2 is needed in a person with an average hair thickness of between 40-60 microns to preserve appearance of the donor region post-surgery. An even higher density is often desired, particularly if multiple surgeries are contemplated when hair thickness falls under 40 microns thickness. Metrics other than a simple preservation of hair density may apply in consideration of the objective of preserving the appearance of the donor region after harvesting of grafts is completed. For example, color of the hair, particularly in relation to color of the donor region may be a factor in some circumstances.

One known technique for automated selection of grafts for harvesting is a completely random selection. There are drawbacks to random selection. One drawback is an inability to guarantee that the selection is distributed more-or-less evenly across the donor region. Indeed, with random selection, it is possible that the harvested follicular units are inadvertently clustered into a small number of groups, giving a splotchy and uneven appearance post-surgery. Another drawback is the possibility that visible patterns are inadvertently generated by the wounds from excised grafts, such as visible lines or spirals or other artifacts formed by the wounds. A further drawback in the context of graft-on-demand processing is the need for dramatic and potentially large repositionings of the harvesting arm in response to the randomness of the selection, whereby the next randomly selected candidate is not near to the current excision.

Thus, automated selection of grafts for harvesting should provide for a generally even selection of grafts across the donor region, but with enough irregularity to ensure that the residual wounds from excised grafts do not form visible patterns. In addition, a potential advantage is to minimize movement of the harvesting arm in response to selection of a next graft.

Embodiments described herein for automated selection of grafts generate disturbed patterns of positions for candidates for graft excision. The patterns are generally evenly spaced across each zone of the donor region, thereby to minimize clustering of harvested grafts. In addition, the patterns are disturbed enough to prevent the formation of visible patterns in the residual wounds. Moreover, the spacing of the disturbed patterns ensures that there is minimal movement of the harvesting arm from one excision to the next. A follicular unit is selected as a harvesting candidate when it is closest in actual position to the generated pattern.

In one embodiment for generating disturbed patterns, a zone-by-zone selection is made for the number of grafts needed from each zone. A regular pattern of lattice grid points, using that number, is defined over the zone. The regular pattern may be rectangular or hexagonal or triangular, or any other suitable regular pattern. Each lattice grid point is then disturbed horizontally and vertically by random amounts. The degree of randomness is proportional to a fraction of the average spacing between the grid points. For example, the degree of randomness may be from around +/−10 percent (%) to +/−40 percent (%) of the average spacing between the grid points, preferably around 20 percent (%) of the average spacing. The distribution of randomness may be a uniform distribution, such as a uniform distribution ranging from −20 to +20 percent (%) of the average spacing between the grid points. For example, if the average spacing of the points in the regular lattice of grid points is around 8.5 mm laterally in each of the horizontal and vertical directions of one zone in the donor region, then the applied randomness should be between 8.5×0.10=0.85 mm and 8.5×0.40=3.40 mm, preferably around 8.5×0.2=1.7 mm, selected individually for each grid point from a uniform distribution. Other distributions may also be considered, such as a Gaussian distribution.

In use, the disturbed pattern of lattice points is superimposed by computer over the donor zone, and follicular units positioned most closely to the lattice points are selected for harvesting.

A separate pattern is generated for each characteristic designated by the surgeon. For example, a separate pattern is generated for 1-hair grafts, for 2-hair grafts, and for 3-or-more hair grafts. Other characteristics, as mentioned above, might include thickness or fineness of the hair(s) in the graft, color of the candidate's hair and skin, width of the candidate hair shafts, and angle of the candidate's hair as it exits in the scalp.

In another embodiment for generating disturbed patterns of positions for candidates for graft excision, a regular pattern of lattice grid points, using the needed number of grafts for a zone, is defined over each zone. In this embodiment, it is not necessary to randomize the positions of the lattice grid points, since the positions of the grid points are disturbed during use. Of course it is also possible to randomize the grid points, as described above, prior to use.

In use, the pattern of lattice points is superimposed by computer over the donor zone, and a first follicular unit positioned most closely to a first lattice point is selected for harvesting. Of course, owing to the natural distribution of follicular units in the zones of the donor region, a candidate follicular unit will not be found exactly at the first lattice point. This is beneficial since it ensures that the candidates are selected with enough irregularity to ensure that there are no visible patterns in the residual extraction wounds.

After selection of the follicular unit positioned most closely to the lattice point, the horizontal and vertical difference between the actual position of the chosen follicular unit and the target position of the lattice is calculated. This positional error is dispersed to an adjacent lattice point or points, so as to disturb the pattern of lattice point. For example, if the harvested follicular unit is positioned to the left of the first lattice point, an adjacent lattice point is disturbed by moving it to the right. In this way, candidates are selected more-or-less evenly across each zone of the donor region, thereby avoiding splotchy appearance of the post-operative donor region, while ensuring that there is enough irregularity in the selection to avoid the formation of visible patterns in wounds left by the excised grafts. In addition, only minor repositionings of the harvesting arm are needed between excisions.

Rather than dispersing the positional error to the very next adjacent candidate, the error may be dispersed using a 1-dimensional or a 2-dimensional kernel to two or more adjacent candidates. For example, the following kernel will disperse half of the positional error to the next adjacent candidate to the right and half to the next adjacent candidate below:

$$\frac{1}{2}\times\begin{bmatrix} \# & 1 \\ 1 & 0 \end{bmatrix}$$

where "#" denotes the candidate currently being processed. Other kernels can be used such as:

$$\frac{1}{6}\times\begin{bmatrix} \# & 3 \\ 2 & 1 \end{bmatrix}$$

which disperses half of the positional error to the next adjacent candidate to the right, one-third to the next adjacent candidate below, and one-sixth to the next adjacent candidate below and to the right.

The above process of generating patterns that are disturbed during use of the pattern is followed independently, on a zone-by-zone basis, for harvesting grafts of follicular units having 3-hairs, 2-hairs and 1-hairs, or for whatever characteristics (such as thickness etc.) that are used to determine candidates for excised grafts.

In describing embodiments of the disclosure herein, specific terminology is employed for the sake of clarity. However, the disclosure herein is not intended to be limited to the specific terminology so selected. The above-described embodiments of the disclosure herein may be modified or varied, without departing from the disclosure herein, as appreciated by those skilled in the art in light of the above teachings. It is therefore to be understood that, within the scope of the claims and their equivalents, the disclosure herein may be practiced otherwise than as specifically described.

The invention claimed is:

1. An apparatus for harvesting hair grafts from a donor region, the apparatus comprising:

a robotic arm having a punch harvesting instrument mounted thereto, wherein the punch harvesting instrument is configured to harvest a follicular unit from the donor region by hand-held or robot-controlled movement of the robotic arm responsive to a command to harvest a follicular unit; an implantation handpiece;

tubing to deliver the harvested follicular unit via suction to the implantation handpiece; and a source of saline or similar biological fluid introduced to the tubing in the vicinity of the punch harvesting instrument to enhance the effect of suction and/or to facilitate delivery of the harvested follicular unit to the implantation handpiece.

2. The apparatus according to claim 1, further comprising one or more cameras positioned to image the donor region, wherein the command to harvest a follicular unit includes a command to harvest a follicular unit with a designated characteristic such as number of hairs, and wherein the robotic arm is moved to a candidate position for harvesting of the follicular unit by reference to a camera image of the donor region.

3. The apparatus according to claim 1, further comprising an implantation robotic arm having the implantation handpiece mounted thereto, wherein the implantation handpiece is configured to implant the follicular unit delivered thereto at a designated implantation site at a recipient region of the scalp by robot-controlled movement of the implantation robotic arm responsive to a command to implant the follicular unit.

4. The apparatus according to claim 1, further comprising a controller constructed such that to harvest a follicular unit, a follicular unit is selected for harvesting by reference to an algorithm that spaces harvested grafts over the donor region in such a way as to minimize areas within the donor region that may become very patchy.

5. The apparatus according to claim 1, further comprising a controller constructed such that to harvest a follicular unit, a follicular unit is selected for harvesting by reference to an algorithm that spaces harvested grafts over the donor region in such a way as to avoid over depletion of grafts from each defined area of the donor region.

6. The apparatus according to claim 1, wherein the command to harvest a follicular unit with the designated characteristic (such as number of hairs) is issued by voice command, and further comprising a controller responsive to the voice command.

7. The apparatus according to claim 1, wherein the command to harvest a follicular unit with the designated characteristic (such as number of hairs) is issued by operation of a foot pedal, and further comprising a controller responsive to operation of the foot pedal.

8. The apparatus according to claim 1, wherein the command to harvest a follicular unit with the designated characteristic (such as number of hairs) is issued by one or more buttons on the implantation handpiece, and further comprising a controller responsive to operation of the one or more buttons.

9. The apparatus according to claim 1, further comprising a controller configured to monitor depletion of hair grafts from the donor region by the number of remaining grafts or the remaining hair mass or the density of the identified areas, and further comprising a display controlled to show a visual depiction of the depletion of hair grafts from the donor region in real time with data quantifying donor density and hair mass numbers.

10. The apparatus according to claim 1, wherein saline is injected into skin in proximity to a graft excision site in a harvesting zone of the donor region, wherein the saline is injected in a general area where harvesting work is being performed by the punch, or is injected specific to the follicular unit targeted for harvesting and excision, such as within 1.0 mm or less of the punch excision site.

11. The apparatus according to claim 1, further comprising an optical system positioned for imaging a harvested graft at an inspection station for automated determination of graft quality as the harvested graft is transported from the donor region to the implantation handpiece.

12. The apparatus according to claim 11, wherein responsive to detection of a graft of poor quality, a notification is provided to alert against implantation of the graft.

13. The apparatus according to claim 12, wherein the notification is an audible alert to the surgeon, to provide the surgeon with the option to discard a graft of poor quality.

14. The apparatus according to claim 12, wherein the notification is a signal to trigger discharge of the graft once the graft reaches the implantation device, so that the graft is not implanted at the recipient area.

15. The apparatus according to claim 12, wherein the notification is an image shown of the graft on the computer monitor, confirming the number of hairs in each graft.

16. The apparatus according to claim 1, further comprising a donor area tensioning pad movable in coordination with movement of the robotic arm so as to apply tension to the scalp in the vicinity of the donor region while harvesting the follicular unit.

17. The apparatus according to claim 16, wherein the donor area tensioning pad is mounted by a flexible arm to the robotic arm for movement in coordination with movement of the robotic arm.

18. The apparatus according to claim 16, wherein the donor area tensioning pad is mounted to a tensioning robotic arm for independent and coordinated movement of the scalp tensioning pad in coordination with movement of the robotic arm.

19. A method comprising using the apparatus according to claim 1 to harvest a hair graft from a donor region and to implant the harvested hair graft to a recipient region.

* * * * *